United States Patent
Craig

(10) Patent No.: US 10,415,022 B2
(45) Date of Patent: *Sep. 17, 2019

(54) TRICHOPLUSIA NI PIGGYBAC TRANSPOSASES WITH REDUCED INTEGRATION ACTIVITY

(71) Applicant: The Johns Hopkins University, Baltimore, MD (US)

(72) Inventor: Nancy L. Craig, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/698,060

(22) Filed: Sep. 7, 2017

(65) Prior Publication Data

US 2018/0072999 A1     Mar. 15, 2018

Related U.S. Application Data

(63) Continuation of application No. 14/233,024, filed as application No. PCT/US2012/046976 on Jul. 16, 2012, now Pat. No. 9,783,790.

(60) Provisional application No. 61/508,386, filed on Jul. 15, 2011.

(51) Int. Cl.
| | | |
|---|---|---|
| *C12N 9/12* | (2006.01) | |
| *C12N 15/85* | (2006.01) | |
| *C12N 15/81* | (2006.01) | |
| *C12N 15/79* | (2006.01) | |
| *C12N 9/22* | (2006.01) | |
| *C12N 15/90* | (2006.01) | |

(52) U.S. Cl.
CPC ............. *C12N 9/1241* (2013.01); *C12N 9/22* (2013.01); *C12N 15/79* (2013.01); *C12N 15/81* (2013.01); *C12N 15/85* (2013.01); *C12N 15/907* (2013.01); *C12N 2800/90* (2013.01)

(58) Field of Classification Search
None
See application file for complete search history.

(56) References Cited

U.S. PATENT DOCUMENTS

| | | | |
|---|---|---|---|
| 9,670,503 B2 * | 6/2017 | Craig | C12N 15/85 |
| 9,783,790 B2 * | 10/2017 | Craig | C12N 9/1241 |
| 2009/0042297 A1 * | 2/2009 | George, Jr. | C12N 15/8509 |
| | | | 435/455 |

FOREIGN PATENT DOCUMENTS

WO    WO-2010/099301 A2    9/2010

OTHER PUBLICATIONS

Chica et al. Curr Opin Biotechnol. Aug. 2005;16(4):378-84.*
Singh et al. Curr Protein Pept Sci. 2017, 18, 1-11.*
Chica, R. A. et al., "Semi-rational approaches to engineering enzyme activity: combining the benefits of directed evolution and rational design," Curr. Opin. Biotechnol., 16(4): pp. 378-384 (Aug. 2005).
Galvin, D. L. et al., "Genome-Wide Mapping of PiggyBac Transposon Integrations in Primary Human T Cells", J Immunotherapy, Oct. 1, 2009, vol. 32, No. 8, pp. 837-844.
Sen, S. et al., "Developments in Directed Evolution for Improving Enzyme Functions," Appl. Biochem. Biotechnol, 143(3): pp. 212-223 (Dec. 2007).
Yusa, K. et al., "A hyperactive piggyBac transposase for mammalian applications", PNAS, Jan. 25, 2011, vol. 108, No. 4, pp. 1531-1536.
Fraser MJ, Ciszczon T, Elick T, Bauser C. Precise excision of TTAA ¬specific lepidopteran transposons piggyBac (IFP2) and tagalong (TFP3) from the baculovirus genome in cell lines from two species of Lepidoptera. Insect Mol Biol. 1996, 5(2):141-51.
Woltjen K, Michael IP, Mohseni P, Desai R, Mileikovsky M, Hamalainen R, Cowling R, Wang W, Liu P, Gertsenstein M, Kaji K, Sung HK, Nagy A. piggyBac transposition reprograms fibroblasts to induced pluripotent stem cells. Nature. 2009, 458(7239):766-70.
Yusa K, Rad R, Takeda J, Bradley A. Generation of transgene-free induced pluripotent mouse stem cells by the piggyBac transposon. Nat Methods. 2009, 6(5):363-9.
Mitra R, Fain-Thornton J, Craig NL. piggyBac can bypass DNA synthesis during cut and paste transposition. EMBO J. 2008, 27(7):1097-109.
Ziegler K, Bui T, Frisque RJ, Grandinetti A, Nerurkar VR. A rapid in vitro polyomavirus DNA replication assay. J Virol Methods. Dec. 1, 2004;122(1):123-7.
Wang W, Lin C, Lu D, Ning Z, Cox T, Melvin D, Wang X, Bradley A, Liu P. Chromosomal transposition of PiggyBac in mouse embryonic stem cells. Proc Natl Acad Sci U S A. Jul. 8, 2008;105(27):9290-5. Epub Jun. 25, 2008.
Harper AL, Skinner LM, Sudol M, Katzman M. Use of patient-derived human immunodeficiency virus type 1 integrases to identify a protein residue that affects target site selection. J Virol. Aug. 2001; 75(16):7756-62.

(Continued)

*Primary Examiner* — Christian L Fronda
(74) *Attorney, Agent, or Firm* — Venable LLP; Keith G. Haddaway; Miguel A. Lopez

(57) ABSTRACT

The present invention is directed to nucleic acid and amino acid sequences of a novel piggyBac transposase enzymes created by modifying the transposase of *Trichoplusia ni*. The piggyBac transposases of the present invention are functionally active or hyperactive for excision and have decreased integration activity compared to wild type *Trichoplusia ni* piggyBac transposase enzyme. These transposases are ideal for use in methods of transforming cells and organisms. In particular embodiments, the present invention provides methods of transient integration and expression of transgenes.

7 Claims, 29 Drawing Sheets

Specification includes a Sequence Listing.

(56) References Cited

OTHER PUBLICATIONS

Maertens GN, Hare S, Cherepanov P. The mechanism of retroviral integration from X-ray structures of its key intermediates. Nature. Nov. 11, 2011; 468(7321):326-9.

Keppler-Ross S, Noffz C, Dean N. A new purple fluorescent color marker for genetic studies in *Saccharomyces cerevisiae* and Candida albicans. Genetics. May 2008;179(1):705-10.

Yusa K, Zhou L, LI MA, Bradley A, Craig NL. A hyperactive piggyBac transposase for mammalian applications. Proc Natl Acad Sci U S A. Jan. 4, 2011, [Epub ahead of print].

Chen YT, Furushima K, Hou PS, Ku AT, Deng JM, Jang CW, Fang H, Adams HP, Kuo ML, Ho EN, Chien CL, Behringer RR. piggyBac transposon-mediated, reversible gene transfer in human embryonic stem cells. Stem Cells Dev. Jun. 2010;19(6):763-71.

Stadtfeld M, Hochedlinger K. Without a trace? PiggyBac-ing toward pluripotency. Nat Methods. May 2009; 6(5):329-30.

\* cited by examiner

```
                                                            D227  D228         D239
Adineta    --GWINEKSRKILIFV-NRSPLESPNIQSYHVKNRFETIISSIQF DNKTAREERKRT DKF 209
Adineta_1  LAGLLGRLRSDLHSLW-RTSPLESPIFKDTISKSRFDKIIACLRF DDKSTREERKKA DKF 202
Anopheles  IRGATESKGMEIDLMW--SEKYGLPFCKNVMSRNRFREIMKFLRF DEKSTRSQRLQT DKF 240
Bombyx     LAGLIKSNRQSLKDLW-RTDGTGVDIFRTTMSLQRFQFLQNNIRF DDKSTRDERKQT DNM 258
Ciona      LTGVVHKRG-KLESYWIKNSMIETPYFGKCMSRNRYQAITGFLHF NDNEKLAENIDN DKL 211
Heliothis  MSGVLRSSHLNFKDLW-ATDGTGIEFFQNTMSFNRFLFISRCVRF DDKNTKSERLKT DKL 232
Takifugu   LAGVFRSKGESAESLW-DAE-TGREIFRATMSLENFHIISRIIRF DNZDDRPARWQR DKL 237
T.ni       MTAVRKDNHMSTDDLF---DRSLSMVYVSVMSRDRFDFLIRCLRM DDKSIRPTLREN DVF 241
                                            D268
Adineta    AVSREIWTDFSRKFKEMYNPGSHGTI DERLLGFRGKCPFRQYIPSKPDKYAIKFWFCVDV 269
Adineta_1  AAIREIWLDFQDKLKTCYTPGLNITI DEQLLGFRGKCPFRQFIPTKPDKYGLKFWLCVDA 262
Anopheles  ALISDVFSRFVSNCQTNYVPGPHISV DEQLFPSKTRCPFTQFMASKPDKYGQKYWMAVDV 300
Bombyx     AAFRSIFDQFVQCCQNAYSPSEFLTI DEMLLSFRGRCLFRVYIPNKPAKYGIKILALVDA 318
Ciona      YKVRPVYDLIVARWKALYNLGEHISI DEGMMKWRGRLGFRVYNKDKPIKYGIKSYILADS 271
Heliothis  AAVREFTDLMNNNFINNYCASENVTL DEQLPAFRGRFSGVVYMPNKPTKYGIKHYALVDS 292
Takifugu   GVIRTVWDKWVRRLPLLYNPGPNVTI DEQLMPFRGRCPFLQYLPSKPAKNGIKIWAACDA 297
T.ni       TPVRKIWDLFIHQCIQNYTPGAHLTI DEQLLGFRGRCPFRMYIPNKPSKYGIKILMMCDS 301
                                                  D346
Adineta    NSYYIFDAFPYIERQP-NEHRQRFVGPNVVLELMKPMYGSNRNVT EDNFFTSIHLAKEL- 327
Adineta_1  ESYYVLNAFPYIGRQP-GQEKQAHVGESVVLELLRPFYGSNRNVT KDNFFTSVPLARNL- 320
Anopheles  DSKYVVNIIPYLGKND-ERPAEERLGDFVVKKLVDPYLNRGRNVT CDNFFTSLELAKFL- 358
Bombyx     KNFYVVNLEVYAGKQPSGPYAVSNRPFEVVERLIQPVARSHRNVT FDNWFTGYELMLHLL 378
Ciona      HSHYCWNLDMYH-------RVQKTLKETVSOILTSKCHFLWHSLYM DNFYNSVSMSQML- 323
Heliothis  ATFYLLKFEIYAGVQPEGPYRMPNDTVSLVKRMTEPIWGTGRNVTM DNWFTSVPLANILL 352
Takifugu   TSSYAWNLQVYTGKPD-GGAPEKNPRNESCPRHVSGTQWTQHH--MRHFFTSHKLGQEL- 353
T.ni       GTKYMINGMPYLGRGTQ--TNGVPLGEYYVKELSKPVHGSCRNIT CDNWFTSIPLAKNLL 359

Adineta    -HSGKLTLVGTLRKNKPEIPIEFQSNKNRDVGSSIFGFS-DNLTLVSYVPKKNKAVILLS 385
Adineta_1  -QTKNLTLIGTLRKNKPEIPIEFLSSKIREIGSSLFGFE-DNLALVSFVPKKNKAVLLLS 378
Anopheles  -KSKKTSLVGTINKARREVPICVKKVKEKLYFTKAFK-S-DDTTLTVYQGKTKKNVVLLS 415
Bombyx     -NEYRLTSVGTVRKNKRQIPESFIRTD-RQPNSSVFGFQ-KDITLVSYAPKKNKVVVVMS 435
Ciona      -LAFQIHSVGTLRSNRGEP-REIRTPPNQMKKGDIIARQNQSVTVLAW---KDKRVVKAI 378
Heliothis  -KDHQLTMVGTIRKNKPEIPTCFQPKRTRTEHSSLFGFQ-EDVTLCSYVPKKSKAVLLIS 410
Takifugu   -LKRKLTIVGTIRKNRSELPPQLLTSKNRPVKSSQFAYT-ADTSLVSYVPKKGKNVVLMS 411
T.ni       QEPYKLTIVGTVRSNKREIPEVLKNSRSRPVGTSMFCFD-GPLTLVSYKPKPAKMVYLLS 418
```

FIG. 1B

```
                                                   D447   D450           W465
Adineta     SMHHDSKV-DI-----------GTGKPNIVLDYNKSKGAVDTIDEMCHKYSVKRGTRRWP 433
Adineta_1   SKHHDNHV-DN-----------KTGKPVIILDYNKTKGAVDTVDQMCHKYTVKRGTKRWP 426
Anopheles   SMHRDIRTGND-----------KKSKPETVAFYNSTKYGVDVVDQMCRKYSLKSASRRWS 464
Bombyx      TMHHDNSIDEST-------G--EKQKPEMITFYNSTKAGVDVVDELCANYNVSRNSKRWP 486
Ciona       STKHDASVTTITRRQRRGGEXESVEKPVCIADYNLHMSGVDQVDQMISYYPCHRKSLKWT 438
Heliothis   SMHNDNNIVES-----------EKKKPEIILYYNSTKGGVDTNDQMCANYNVGRRTKRWP 459
Takifugu    TLHRDGRMCDQ-----------EHHKPEIIMDYNATKGGVDNMDKLVTAYSCKRRTLRWP 460
T.ni        SCDEDASI-NE-----------STGKPQMVMYYNQTKGGVDTLDQMCSVMTCSRKTNRWP 466

Adineta     LCVFYGMIDAAAINAMSLWKKKNPNWNANKKYKRRLFLEELGTLLTSYLLDFRIKNSS-- 491
Adineta_1   LCIFYGMIDMAALNAFILWKSKNPVWNENKRYQRRLFLEELRLSLVTPLLDFRSKTSN-- 484
Anopheles   VHSFFNILDLAGINAWVLYKELT-----KENISRRDFLFKLGEELAEEYVENKSANAN-- 517
Bombyx      MTLFYGVLNMAAINACIIYRTN-----KNVTIKRTEFIRSLGLSMIYEHLHSRNKKKN-- 539
Ciona       KKVFFYFMTISVHNAYILYKSKS-----SA--KSCKTLYSFILTLVSQLCQQDRLQPQ-- 489
Heliothis   MVIFYHLLNVAGINAYVIFKNK-----IDHGISRREFLKHLAVDLVKVHQQTRSNIPQ-- 512
Takifugu    LVIFFDMLDISAYNAFVIWMALNPEWKRVKLQKRRLFLEDLGKALVRPQIERRKHIPRTP 520
T.ni        MALLYGMINIACINSFIIYSH-NVSSKGEKVQSRKKFMRNLYMSLTSSFMRKRLEAPT-- 523
                                                              C558    C561
Adineta     ---TLHKDIQ--NALVRFGYPRIETELE----TFVTDSARSKRKRCSLCDYSSDRKVSNT 542
Adineta_1   ---FLHKDIQ--NALLIVGHPVSKRDSQ----KSDEDSAQSKRKRCSICETSKDRKTSNK 535
Anopheles   ---LPM--------------------------TNAGGSRRRYKVQTSCHEGKSANE 544
Bombyx      ---IPTYLRQ--RIEKQLGEPSP---------RHVNVPGRYVRCQDCPYKKDRKTKRS 583
Ciona       ---IDD-------ENLAGPPPKSPRIDS----TKRLKGGFKKHVIALYPPTKKKAAAQRP 535
Heliothis   ---LP-RAVQ--KRLKR---NAEVQDPG----STSRGGPSTSYKRCHICPRSKDKKIRFM 559
Takifugu    ASAAMVRRIQKENAGALSTQPTEPQSAEPEVNVZXVVNSSNKKKRCEVCGPKMDRKTQYT 580
T.ni        ---LKRYLRD--NISNILPNEV-PGTSD----DSTEEPVMKKRTYCTYCPSKIRRKANAS 573
            C574 C577 C582 H585   C590 C593
Adineta     CYKCSEPICKQHSMK-RVFRINCSK------ 566
Adineta_1   CYNCSAFVCSEHCVK-QIFCINCSK------ 559
Anopheles   CFTCNRPVCKKCTKRISYVCVSCEPGSDEAM 575
Bombyx      CNACAKPICMEHAK---FLCENCAE-LDSSL 610
Ciona       CRACMKNGCRKDTIL---L------------ 551
Heliothis   CAKCHHHICHDHST---MICDKCID------ 581
Takifugu    CIKCKKYICNTHTVK---LWPSCVV------ 602
T.ni        CKKCKKVICREHNID---MCQSC-F------ 594
```

FIG. 1B
CONTINUED

| | Excision | Integration |
|---|---|---|
| piggyBac WT | +++++ | +++++ |
| R245A | +++++ | ++ |
| R275A/ R277A | +++++ | - |
| R315A | +++++ | +++++ |
| S351E | ++++ | ++/- |
| R341A | +++++ | +++/- |
| K375A | +++++ | ++++ |
| R372A/ K375A | +++++ | - |
| R388A | +++++ | - |
| K409A/ K412A | +++ | +++/- |
| K432A | +++ | +++ |

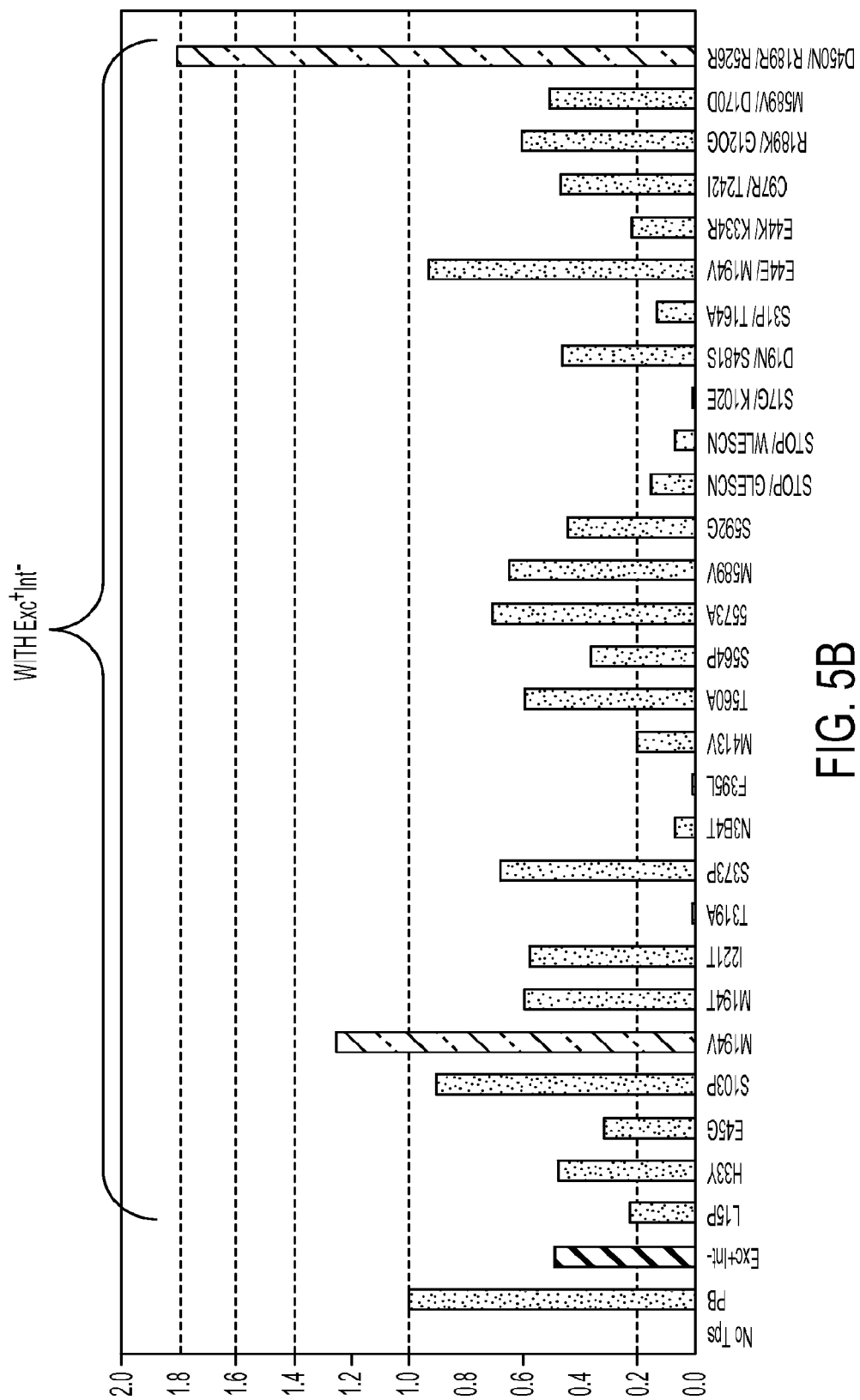

| Position | 30 | 103 | 165 | 194 | 282 | 450 | 509 | 538 | 571 | others |
|---|---|---|---|---|---|---|---|---|---|---|
| HP-1  | + | + | - | + | - | - | - | - | - | |
| HP-3  | + | - | + | + | - | - | + | + | + | Stop to W |
| HP-5  | + | + | - | + | - | - | - | + | + | |
| HP-8  | + | + | + | + | - | - | - | + | + | |
| HP-17 | - | - | - | + | - | - | + | + | + | |
| HP-21 | - | - | + | + | - | - | - | - | - | |
| HP-24 | - | - | + | + | - | - | - | - | - | L235H, CTT CAT |
| HP-30 | + | + | + | + | - | - | - | + | + | |
| HP-38 | + | + | + | + | - | - | - | + | + | |
| HP-39 | + | + | + | + | - | - | - | - | + | |
| HP-41 | + | + | + | + | - | - | - | - | + | |
| HP-42 | + | + | + | + | - | - | - | - | + | E45K |
| HP-43 | + | + | - | + | - | - | - | + | + | |
| HP-48 | - | - | + | + | - | - | - | - | - | F594L |

| Position | 30 | 103 | 165 | 194 | 282 | 450 | 509 | 538 | 571 | others |
|---|---|---|---|---|---|---|---|---|---|---|
| Mi-9  | − | + | + | + | + | − | − | − | + | |
| Mi-10 | + | + | + | + | + | − | + | + | + | |
| Mi-11 | + | + | + | + | + | − | + | + | + | |
| Mi-13 | + | + | + | + | + | − | + | + | + | |
| Mi-15 | + | + | + | + | + | − | − | − | + | |
| Mi-25 | + | − | − | − | − | + | − | + | + | F594L |
| Mi-31 | + | + | + | + | + | − | + | + | + | F594L |
| Mi-45 | − | + | + | + | + | − | − | − | + | |
| Mi-50 | − | + | + | + | + | + | + | + | − | F594L |

Mi10 = Mi11 = Mi13 = 7PB/ M194V/ Exc+Int-
Mi15 = M45 = 103/165/194/282/571/ Exc+Int-
M31 = 7PB/D450N/F594L

FIG. 9B

| Position | 30 | 103 | 165 | 194 | 282 | 450 | 509 | 538 | 571 | others |
|---|---|---|---|---|---|---|---|---|---|---|
| Low-2  | + | − | + | − | − | − | − | − | + | |
| Low-3  | − | + | + | + | + | − | − | − | − | |
| Low-6  | − | − | − | + | + | − | + | + | + | |
| Low-7  | + | + | + | + | + | − | − | − | − | |
| Low-9  | + | + | + | + | + | − | − | − | + | |
| Low-10 | + | − | − | − | − | + | − | − | − | |
| Low-16 | + | − | + | + | − | + | + | − | + | |
| Low-17 | + | + | + | + | + | + | + | + | + | template |
| Low-22 | − | − | − | − | + | + | + | − | − | |
| Low-26 | + | + | − | − | + | + | + | + | + | |
| Low-27 | − | − | − | − | − | − | − | + | + | |

FIG. 9C

TRICHOPLUSIA NI PIGGYBAC TRANSPOSASES WITH REDUCED INTEGRATION ACTIVITY

CROSS-REFERENCE TO PRIOR APPLICATIONS

This application is a continuation of U.S. patent application Ser. No. 14/233,024, filed on 15 Jan. 2014, which claims the benefit of U.S. Provisional Application No. 61/508,386, filed on 15 Jul. 2011, the entire contents of each are incorporated herein by reference to the extent permitted by applicable law and regulation.

U.S. GOVERNMENT SUPPORT

Not Applicable

SEQUENCE LISTING

The instant application contains a Sequence Listing which has been transferred from related U.S. patent application Ser. No. 14/233,024, filed on 15 Jan. 2014 and is hereby incorporated by reference in its entirety. Said Sequence Listing was previously submitted in ASCII format via EFS-WEB in said related application. Said ASCII copy was created on Oct. 10, 2016, was named "02240-360866_SL.txt" and is 15,713 bytes in size.

BACKGROUND OF THE INVENTION

The ability to generate induced pluripotent stem cells (iPSCs) without a permanent DNA sequence change is extremely important for many subsequent applications. A useful strategy is to integrate the genes necessary for transformation into the target genome using the DNA cut & paste piggyBac transposon (1) as the vector. The piggyBac transposon has a large cargo size and a high integration efficiency. The piggyBac transposase promotes insertion of the piggyBac transposon into TTAA target sites by binding to specific sequences at the transposon ends. Upon integration, the element becomes stably associated with the host genome and can serve as a long-term source of transcription factors required for cell transformation. Once iPS cell transformation has occurred, the piggyBac vector can then be re-exposed to transposase and excised by its natural "precise excision" pathway, in which the insertion site is restored to its pre-transposon TTAA sequence (2, 3). To avoid further genome modification, it is important that the excised transposon not re-integrate.

We are interested in developing improved piggyBac transposons as more useful tools for generating transgene-free iPSCs. A particularly useful tool for removal of the piggyBac vector after iPS cells transformation would be a piggyBac transposase that can promote excision at high frequency but is defective for re-integration following excision, i.e., an Exc$^+$Int$^-$ transposase.

Using in vitro and in vivo assays in mammalian cells (4), we have isolated a piggyBac Exc$^+$Int$^-$ transposase. In *Saccharomyces cerevisiae* (4), and confirmed in mammalian cells, we have also isolated a transposase that is hyperactive for excision but still integration negative, Exc$^{+hyper}$Int$^-$.

DESCRIPTION OF THE FIGURES

FIGS. 1A and 1B are sequence alignments of the *T. ni* transposase sequence with other transposases in the same protein family.

FIG. 2C is a table of the excision and integration activities;

FIG. 4B shows the retest of the relative excision activities of the hyperactive mutants.

FIG. 5B shows the relative activities of the candidates.

FIG. 9A is a table showing mutation combinations with hyperactive excision; FIG. 9B is a table showing mutation combinations with WT-like excision activities; and FIG. 9C is a table showing mutation combinations that give low excision activities.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide unique Ext+Int− transposases.

Transient integration and expression of transcription factors are important approaches to generate transgene-free iPSCs as well as directed differentiation tissues for both research and clinical use. Removal of the transgenes is critical for the therapeutic applications of the iPSCs. The piggyBac transposon, which was isolated from cabbage loop moth, *Trichoplusia ni*, can efficiently transpose genes of interest into the mammalian genome and more importantly can be precisely removed from the integration sites by piggyBac transposase thereby restoring the original sequence at integration sites. However, reintegration of the excised transposon catalyzed by the transposase is a concern (with piggyBac about 40-50% of the excised transposons reintegrate (6)). A piggyBac transposase mutant, which can only excise without integration would be a useful tool for generating iPSCs without any genetic change.

To that end, we screened a piggyBac transposase target knockout for mutations, which could only catalyze the excision of the transposon but not integration. We further looked for increased excision activity by screening for hyperactive mutants, while still maintaining the integration negative feature.

Excision+Integration− Mutant Screening In Vivo and In Vitro.

Figure 1A:
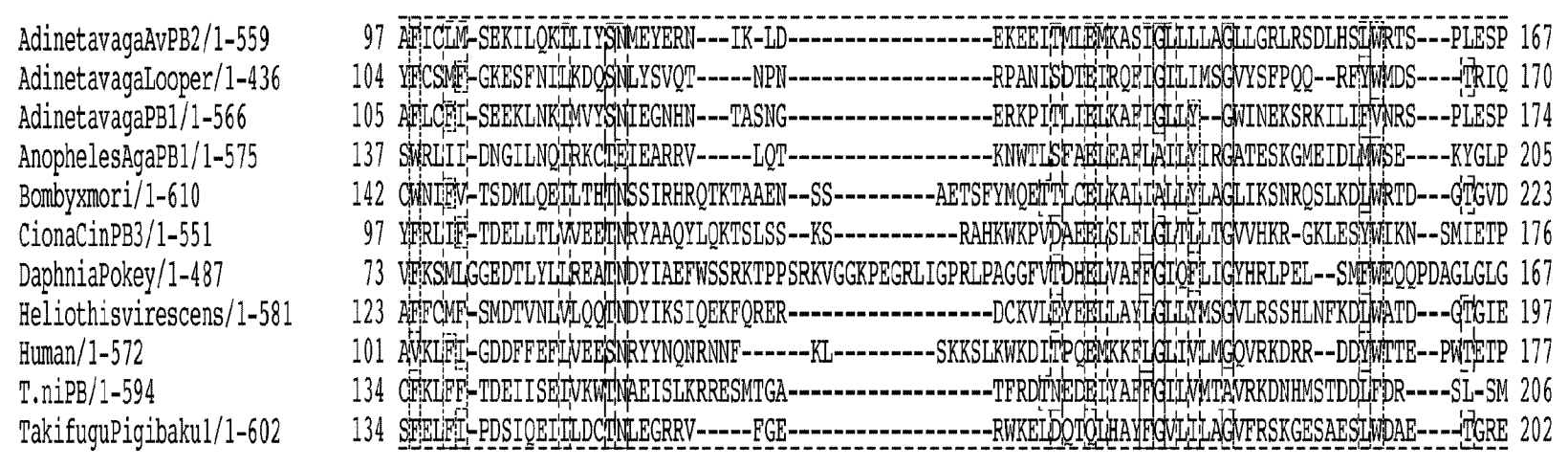
Figure 1A:
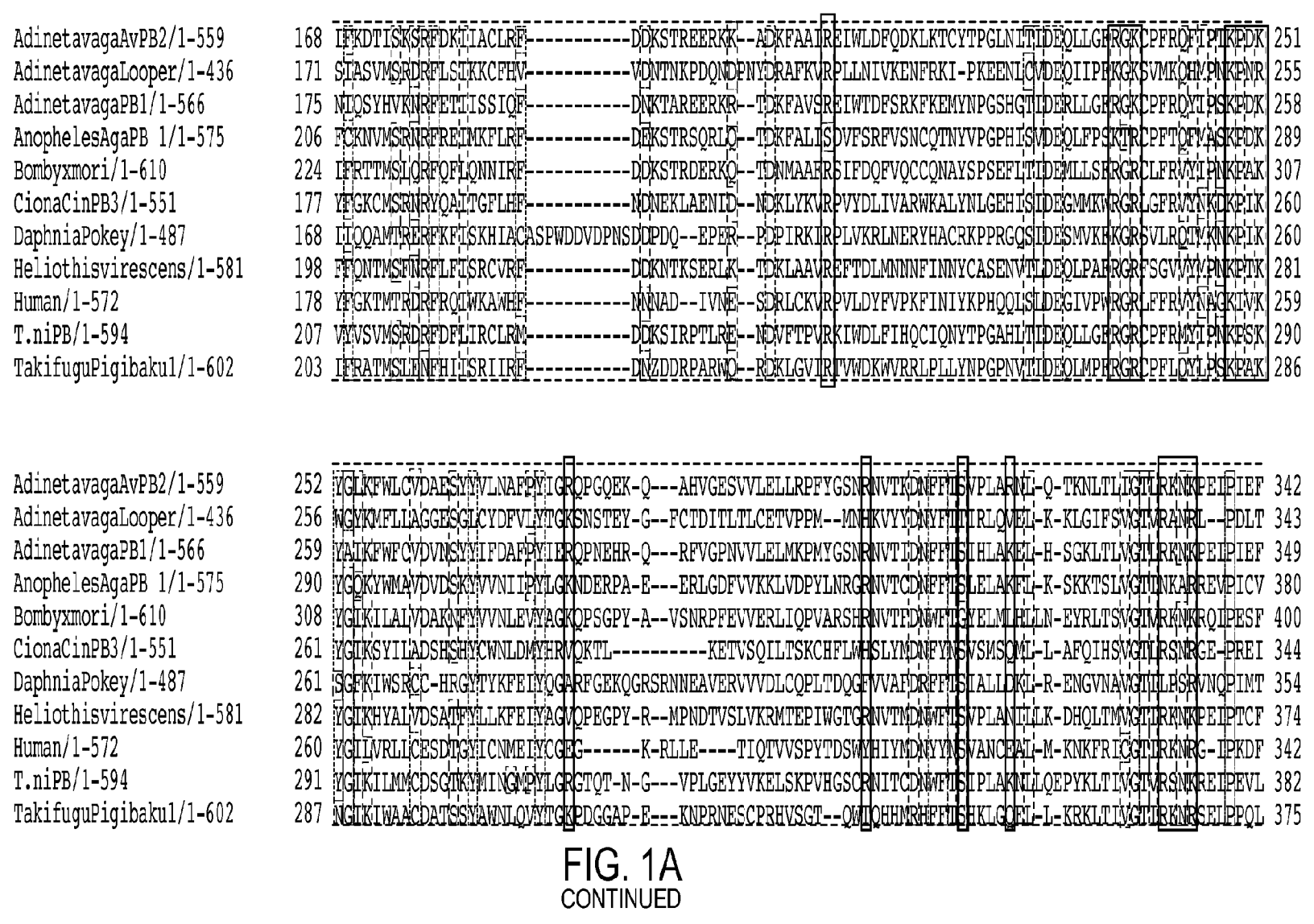
Figure 1A:
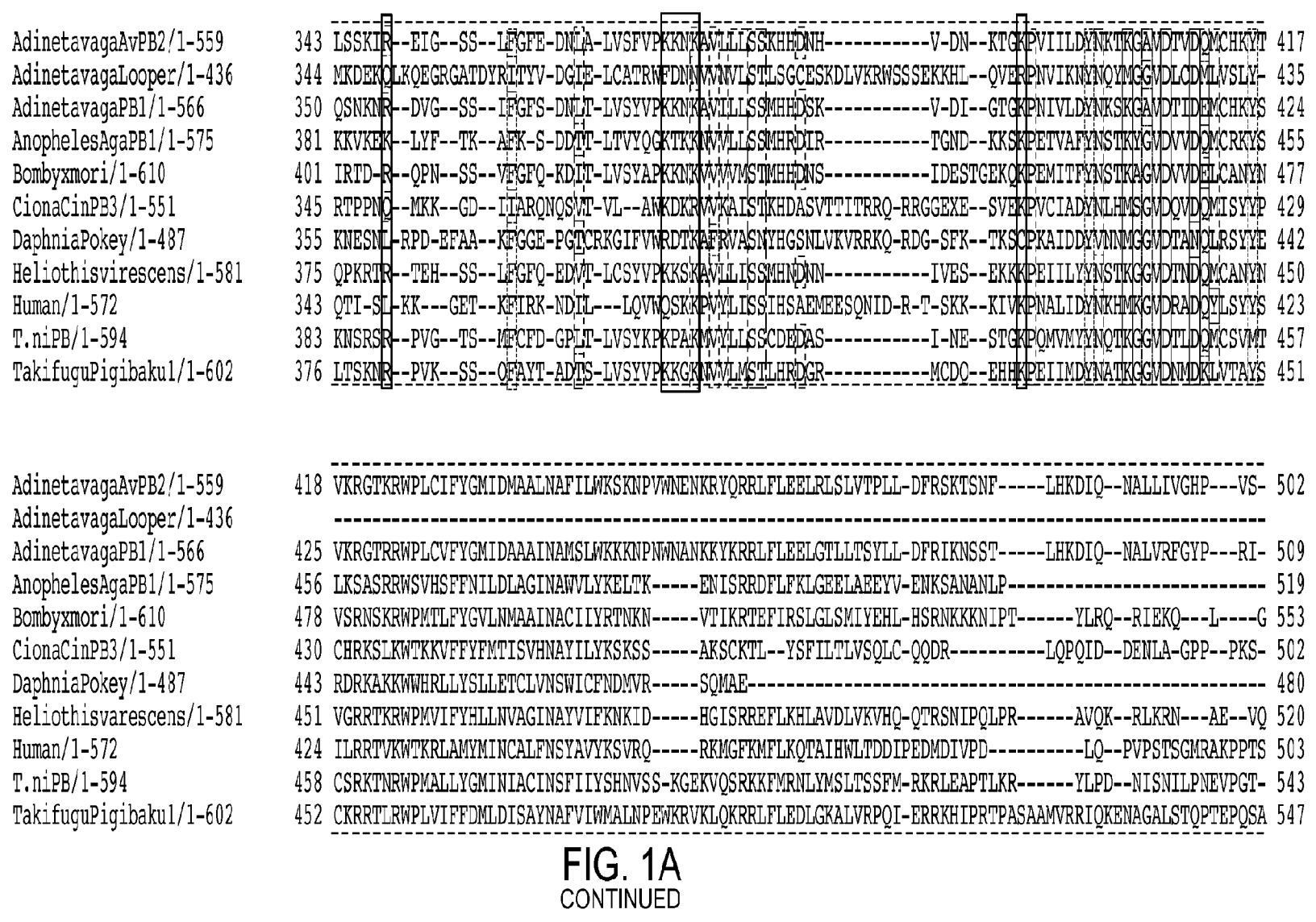
Figure 1C:
FIG. 1C shows the important mutagenized sites of *T. ni* transposase (SEQ ID NO:52).

The alignment of the piggyBac family showed that there are some conserved arginines and lysines around the catalytic sites D268, D346 and D447. We mutated these Arg and Lys to Ala. At the same time, we also mutated the other two amino acids, which are located at the conserved second catalytic D of HIV integrase I and asked whether the excision and integration activities of these mutants are abolished. FIGS. 1A, 1B and 1C show the amino acid residues chosen for making excision+/integration− (Exc+ Int−) mutation, R245A, R275A/R277A/K287A, K287A/ K290A, R315A, R341A, S351E, K356E, K375A, R372A/ K375A/R388A, K409A/K412A, K432A, R460A/K461A. FIG. 1C shows the amino acid sequence of wild-type *Trichoplusia ni* piggyback transposase: GILVMTAVRKD-NHMSTDDLFDRSLSMVYVSVMSRDRFDFLIRCL-RMDDKSIRP TLRENDVFTPVRKIWDLFIHQCIQNYT-PGAHLTIDEQLLGFRGRCPFRMYIPNKP SKYGIKILMMCDSGTKYMINGMPYLGRGTQTNGV-PLGEYYVKELSKPVHGSCR NITCDNWFTSIPLAKN-LQEPYKLTIVGTVRSNKREIPEVLKNSRSR-PVGTSMFC FDGPLTLVSYKPKPAKMVYLLSSCDEDASINESTGK-PQMVMYYNQTKGGVDTL DQMCSVMTCSRKT-NRWPMALLYGMINIACINSFIIYSHNVSSKGEKVQS-RKKFM RNLYMSLTSSFMRKRLEAPTLKRYLRDNISNILPNEV (SEQ ID NO:52). To test the excision activity in vitro, we co-transfected the transposase plasmids, either wild type (WT) or different mutants made by site-direct mutagenesis, together with the donor plasmid which carries piggyBac transposon into HEK293 cells with FuGENE 6 transfection reagent.

Figure 2A:
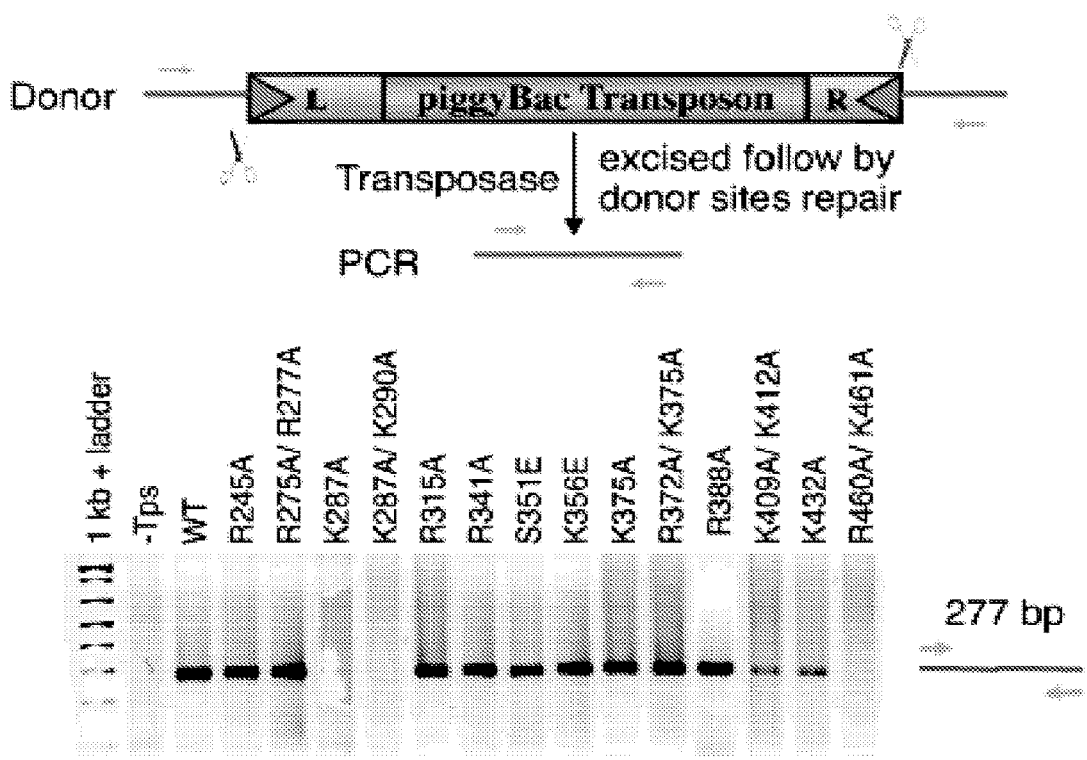
FIG. 2A shows an excision assay by PCR.
Figure 2B:
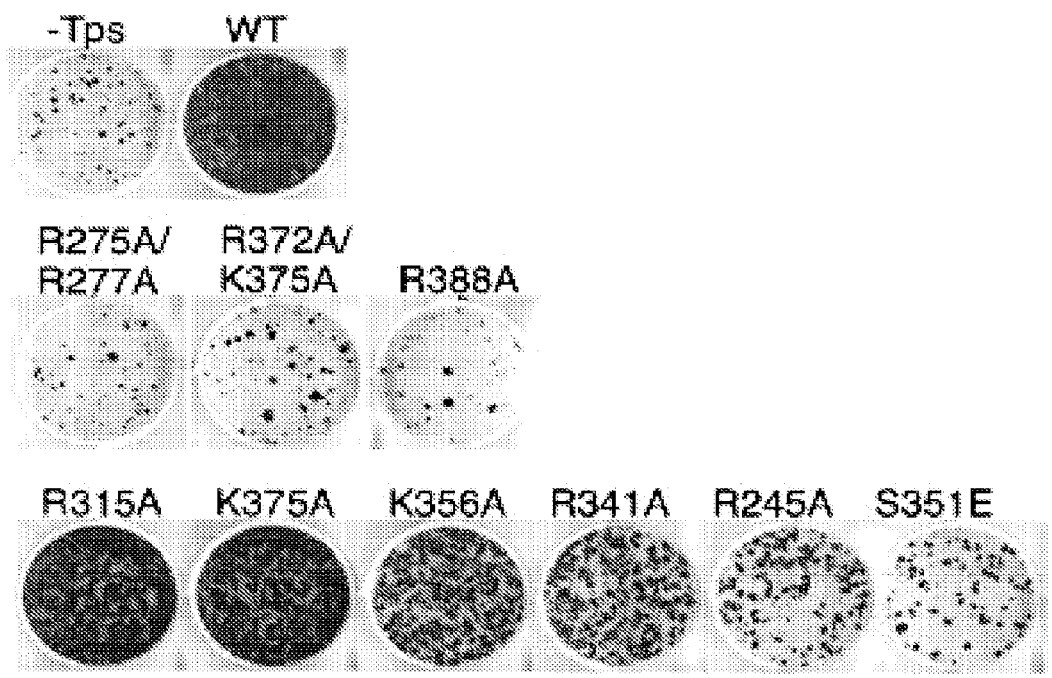
FIG. 2B shows results of colony counting assays.

Three days after transfection, the cells were harvested and plasmids were recovered by Hirt methods as described in (5). PCR was then completed with 2 primers against the flanking donor sites (pbexl2, GGAACAGGAGAGCGCAC-GAG [SEQ ID NO:1] and pbexr2, GAGAGTGCAC-CATATATGCGGTG [SEQ ID NO:2]) using the following conditions (I×95° C., 4 min; 40×94° C., 30 sec, 64° C., 30 sec and 72° C., 30 sec; I×72° C., 5 min). PCR products were run on 1.8% agarose gel and results were shown by ethidium bromide (EtBr) staining. FIG. 2A shows the excision assay strategy and FIG. 2B shows the results of PCR products from repaired donor DNA after excision. A shorter (277 bp) DNA fragment is shown on the gel if there is excision and the donor side repaired. As shown in FIG. 2B, R245A, R275A/R277A, R315A, R341A, S351E, K356E, K375A, R372A/K375A, R388A showed excision activity at similar level to WT. K409A/K412A and K432A showed decreased excision activity. No excision activity was observed with K287A, K287A/K290A, (F349A) and R460A/K461A either due to abolished excision activity or to flanking donor sites that cannot be repaired. We were interested in the mutants with WT excision activity and wanted to know whether they are defective in the integration step. Colony counting assays were used to test the integration activity of the mutants. HeLa cells were co-transfected with donor plasmid containing piggyBac transposon carrying blasticidin drug resistance marker and transposase (both WT and mutants) expression plasmids.

Two days later, cells were trypsinized, diluted and seeded on plates with DMEM medium containing 3.5 ug/ml blasticidin. Drug selection was continued for 18 to 21 days, surviving cells were stained with 0.2% methylene blue, and the plates were scanned. As shown in FIG. 2C, R275A/ R277A, R372A/K375A and R388A have no integration activity (same level as the negative control without transposase) or very low integration activity. Interestingly, S351E showed very low integration activity. S351 is conserved with the Ser119 of HIV integrase I (7) and in a recently solved PFV integrase structure (8), A188 follows the conserved second catalytic D site. Both amino acids are reported to be important for integrase targeting. K356A, R341A and R245A showed decreased integration activity. R315A and K375A showed little change in integration activity as compared with WT.

Thus, we have several mutant candidates for further study: namely, R275A/R277A, R372A/K375A, R388A and S351E. We also included two mutants with dramatic decreases in integration activity: R341A and R245A. To better understand the mechanism, we performed in vitro assays with proteins purified from an *Escherichia coli* strain having an over-expressed transposase.

In Vitro Characterization of the Exc+/Int− (or Int Decreased) Mutants.

Figure 3A:
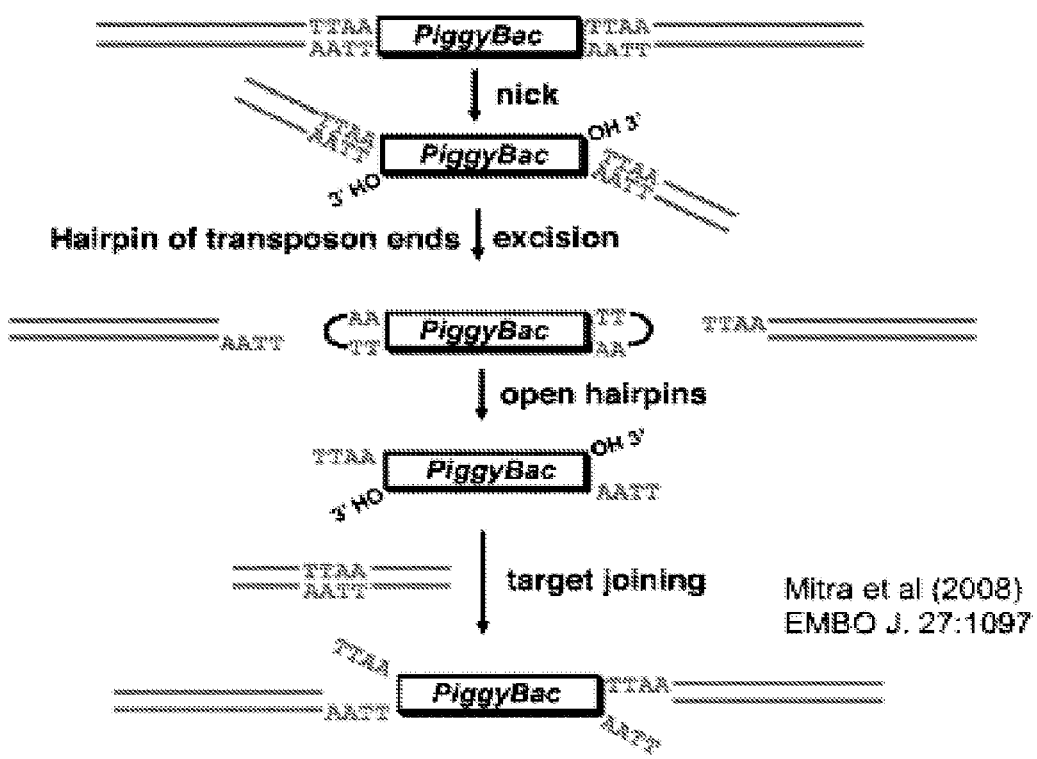
FIG. 3A is a diagram of the steps of the piggyBac transposon operation.

It has been shown that piggyBac transposase catalyzes the transposition in 4-steps (4) as shown in FIG. 3A: 1) in vitro nick; 2) hairpin of transposon ends excision; 3) opening of hairpins formed after a double-strand break; and 4) target joining. We know that the excision activity of R275A/ R277A, R372A/K375A, R388A, S351E, R341A and R245A mutants is about the same level as WT, this means that nick, hairpin formation and double-strand break steps should be about the same as WT. We started from the hairpin opening/resolution step to see whether they show differences in hairpin opening and/or target joining. To test the kinetics of the hairpin resolution step of different mutants, we used a 5'-$^{32}$P-labeled PGB40, a 35 base pair (bp) hairpin with extra TTAA (74 nucleotide (nt) oligo containing 35 bp of PB L-end and flanking TTAA in the middle (PGB40: CAT-GCGTCAATTTTACGCAGACTATCTTTCTAGGGT-TAACCCTAGAAAGATA GTCTGCGTAAAATTGACG-CATG [SEQ ID NO:3]).

Figure 3B:
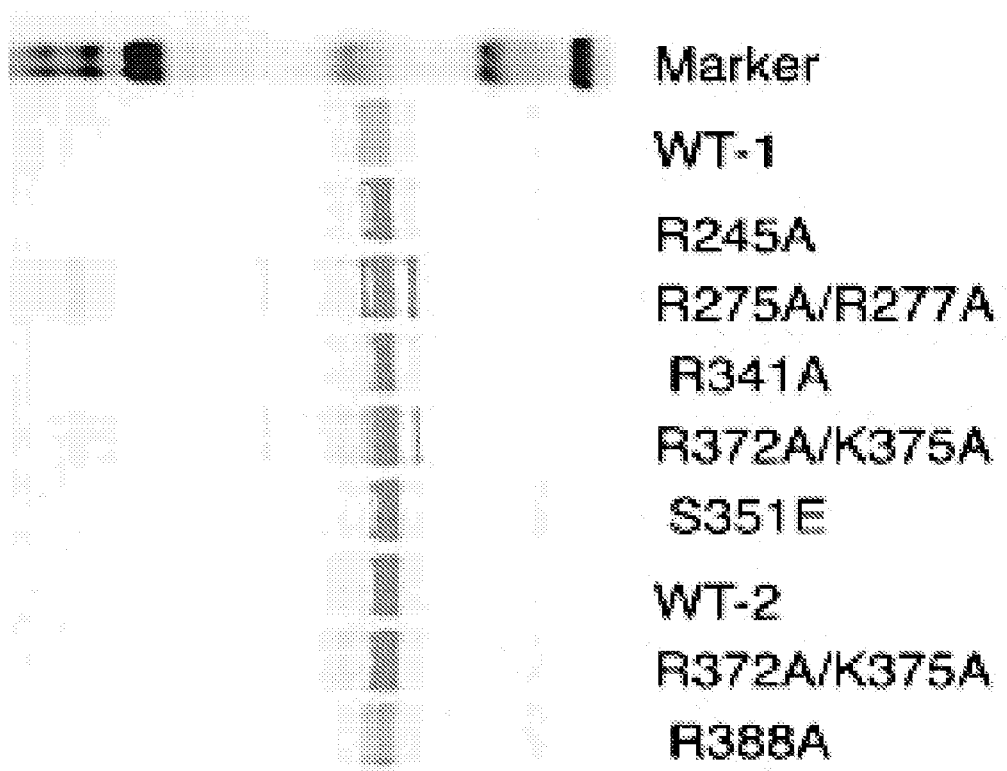
FIG. 3B shows gels of the purified proteins from the various candidates.
Figure 3C:
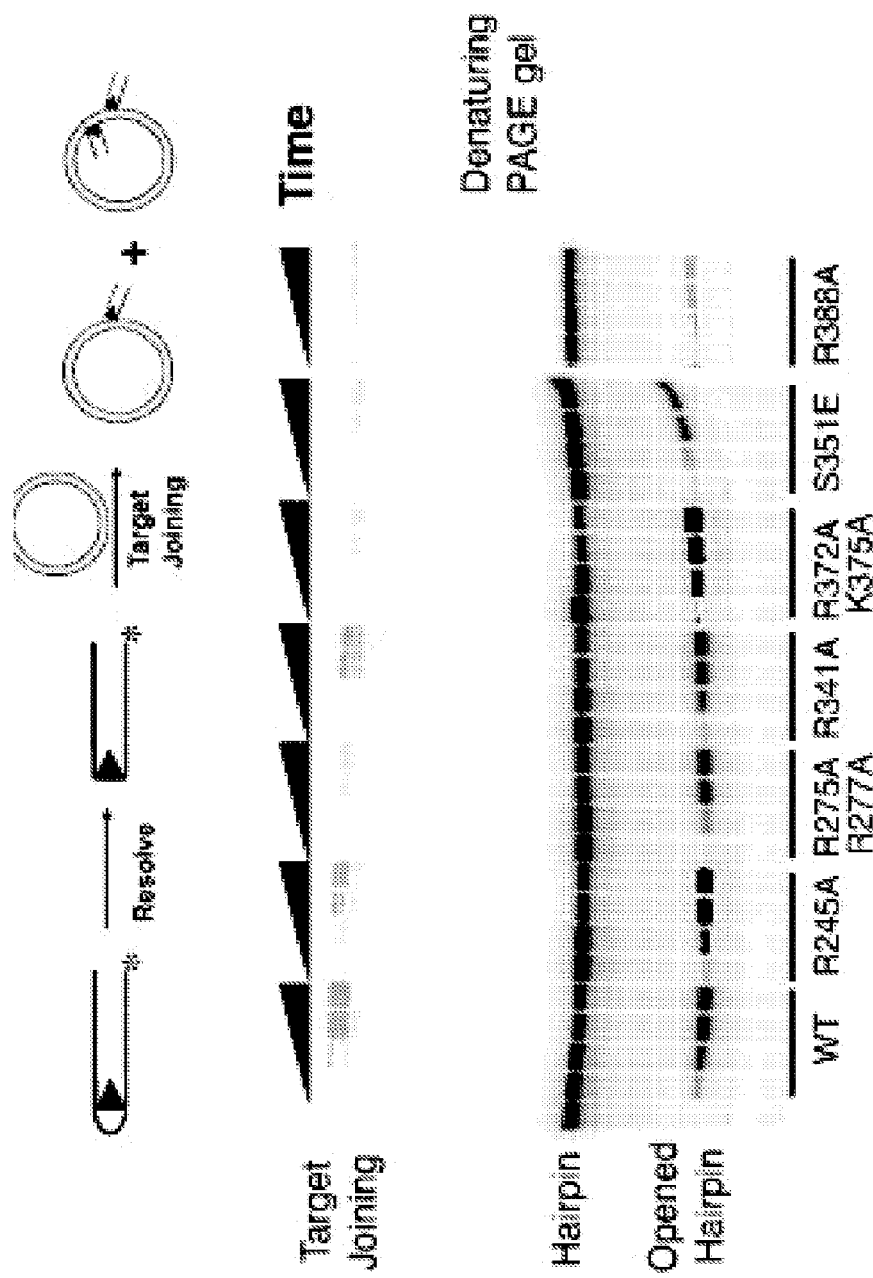
FIG. 3C shows the results of the hairpin resolving and target joining assay.
Figure 3D:
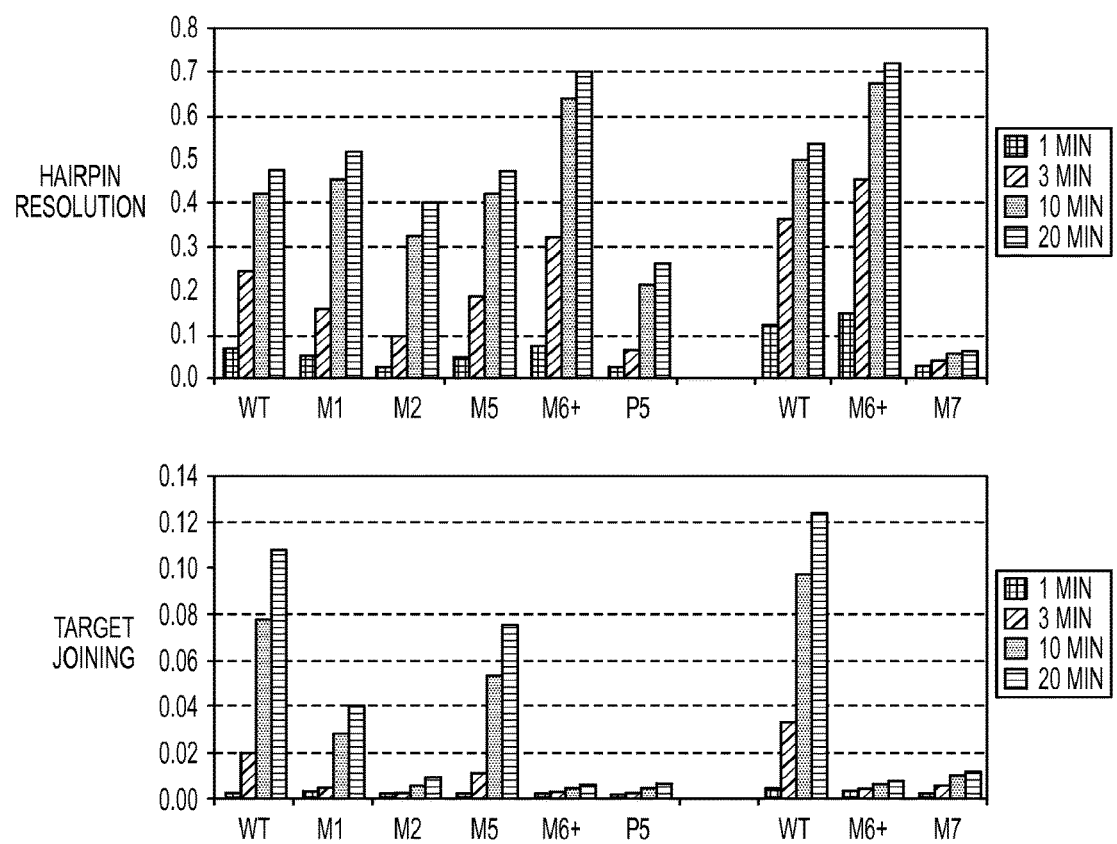
FIG. 3D are charts showing quantification of the tests in FIG. 3C.
Figure 3E:
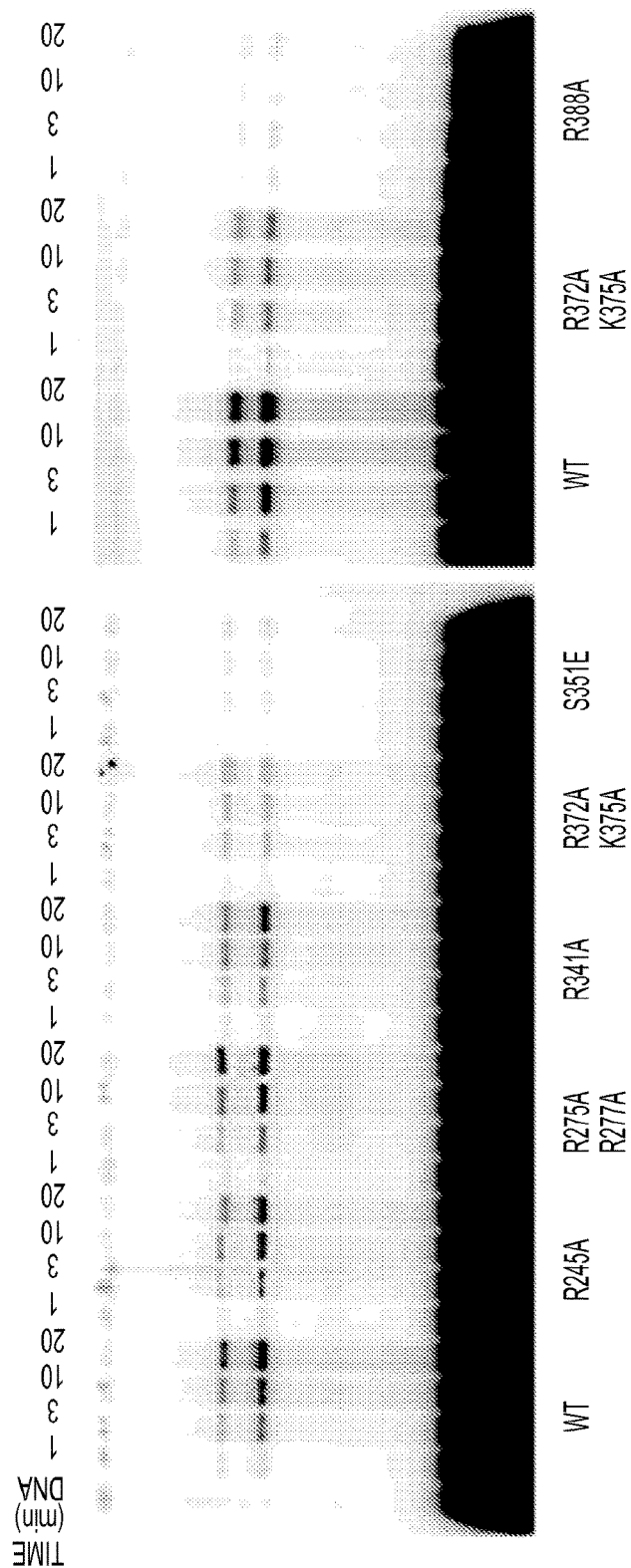
FIG. 3E shows gels depicting the results of the strand transfer assay.
Figure 3F:
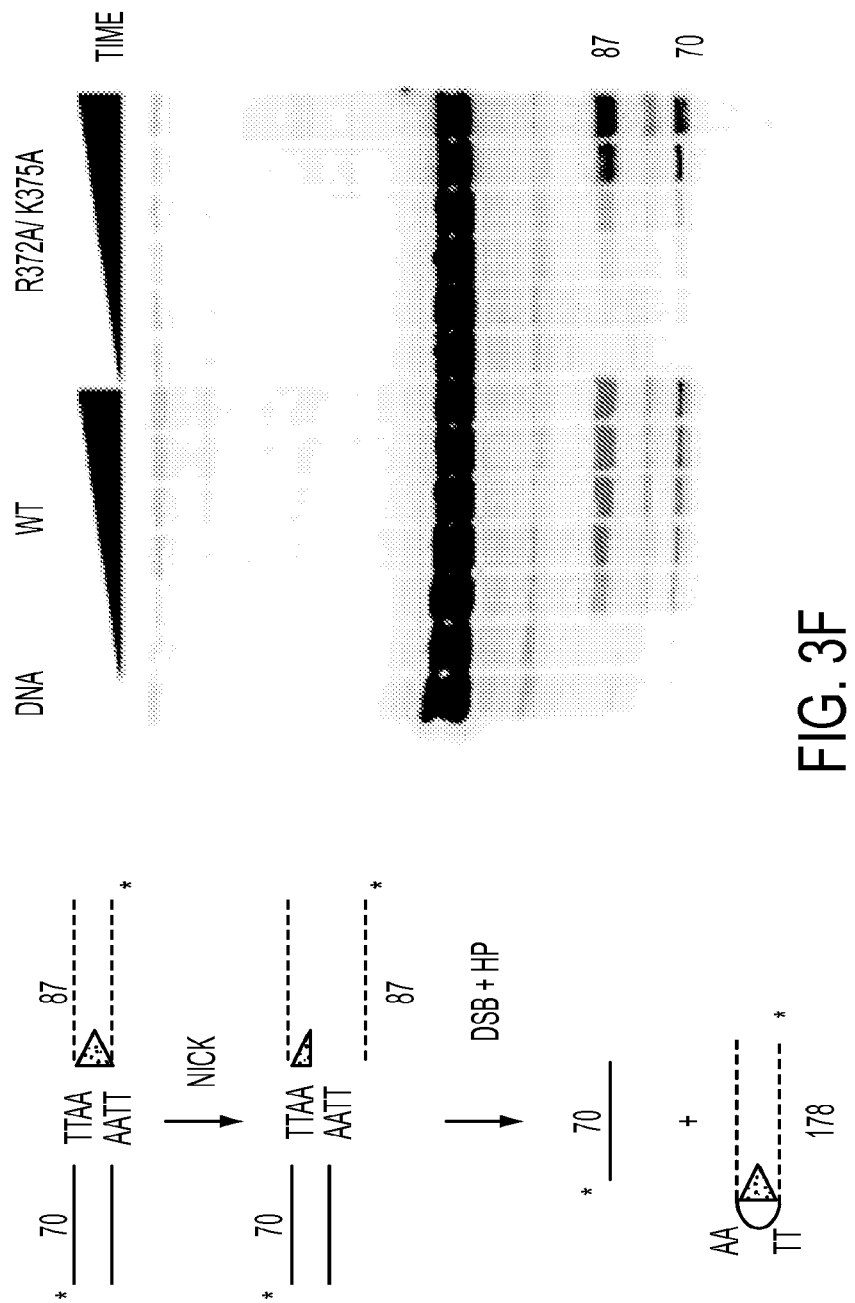
FIG. 3F shows the results of an assay for in vitro nick (at 87 nt) and double strand breaks (at 70 nt).

FIGS. 3A-3F show the details of the assays. FIG. 3B shows a gel of the Int− proteins. FIG. 3C shows the results of the hairpin resolved and target joining assay. A 60-bp R-end oligo with TTAA hairpin was labeled with $^{32}$P at the 5'-end used as substrate and reactions were performed as previous described (4), reactions were stopped at different time points by adding EDTA. Samples were run on denaturing PAGE gel. If the hairpin is opened, it will give a shorter (35 nt) DNA fragment on a denaturing sequencing gel. From the reaction, we can also observe target joining products if this step is not defective for the mutants. As shown in FIGS. 3E and 3F, R372A/K375A has better hairpin resolving activity as compared with WT, but is defective in target joining. R275A/R277A and S35 1E showed slightly decreased in hairpin resolving, and were defective in target joining. R388A showed dramatic decrease in hairpin opening/resolving and was therefore defective in target joining. The other two mutants—R245A and R341A showed a slight decrease in both hairpin resolving and target joining, which suggest that R245 and R341 are not involved in targeting step. This in vitro data agrees with the in vivo data shown previously. Based on both in vivo and in vitro data, we chose R372A/K375A further studies as the best candidate for piggyBac transposase mutants with excision plus and integration minus features (Exc+/Int−).

To better understand the kinetics of the R372A/K375A mutant, we performed a nick and double-strand break assay with a DNA substrate containing 74 bp flanking sequence with TTAA and 87 bp of piggyBac R-TIR and labeled it at 5'-end of both top and bottom strands (FIG. 3F). The results showed that the R372A/K375A mutant has slower nick and double-strand break activity in pre-steady state. However, at steady state, R372A/K375A mutant has comparable double strand break products accumulated but cannot further form the target joining product. In the case of WT, partial double strand break products can transform into target joining product.

In Vivo Excision Assay in Yeast, *Saccharomyces cerevisiae*.

Figure 4A:
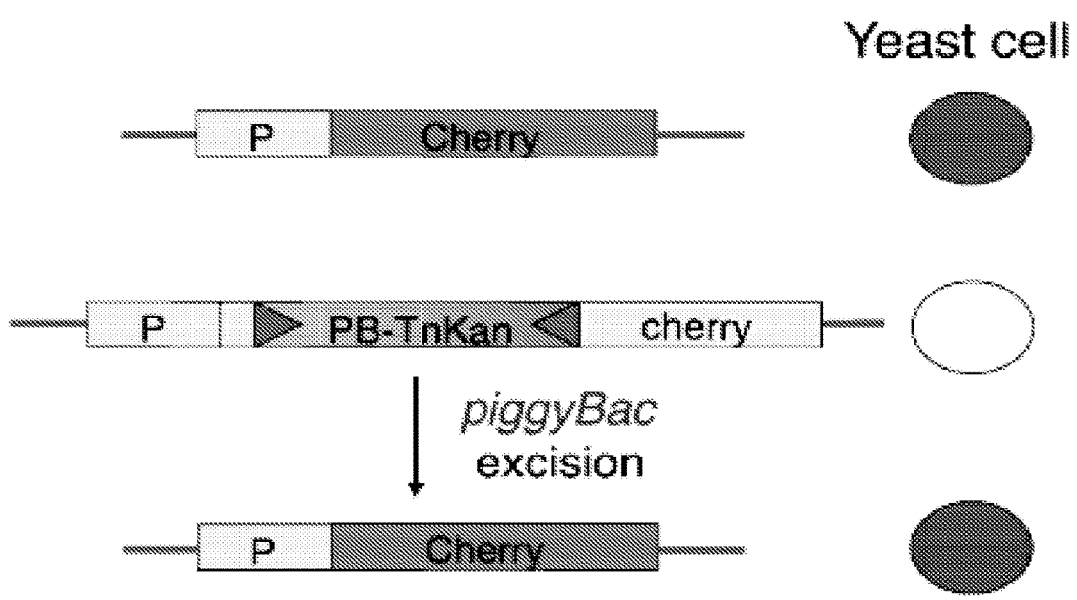
FIG. 4A is a diagram of the process related to the color from the Cherry gene of the yeast cell.
Figure 4B:
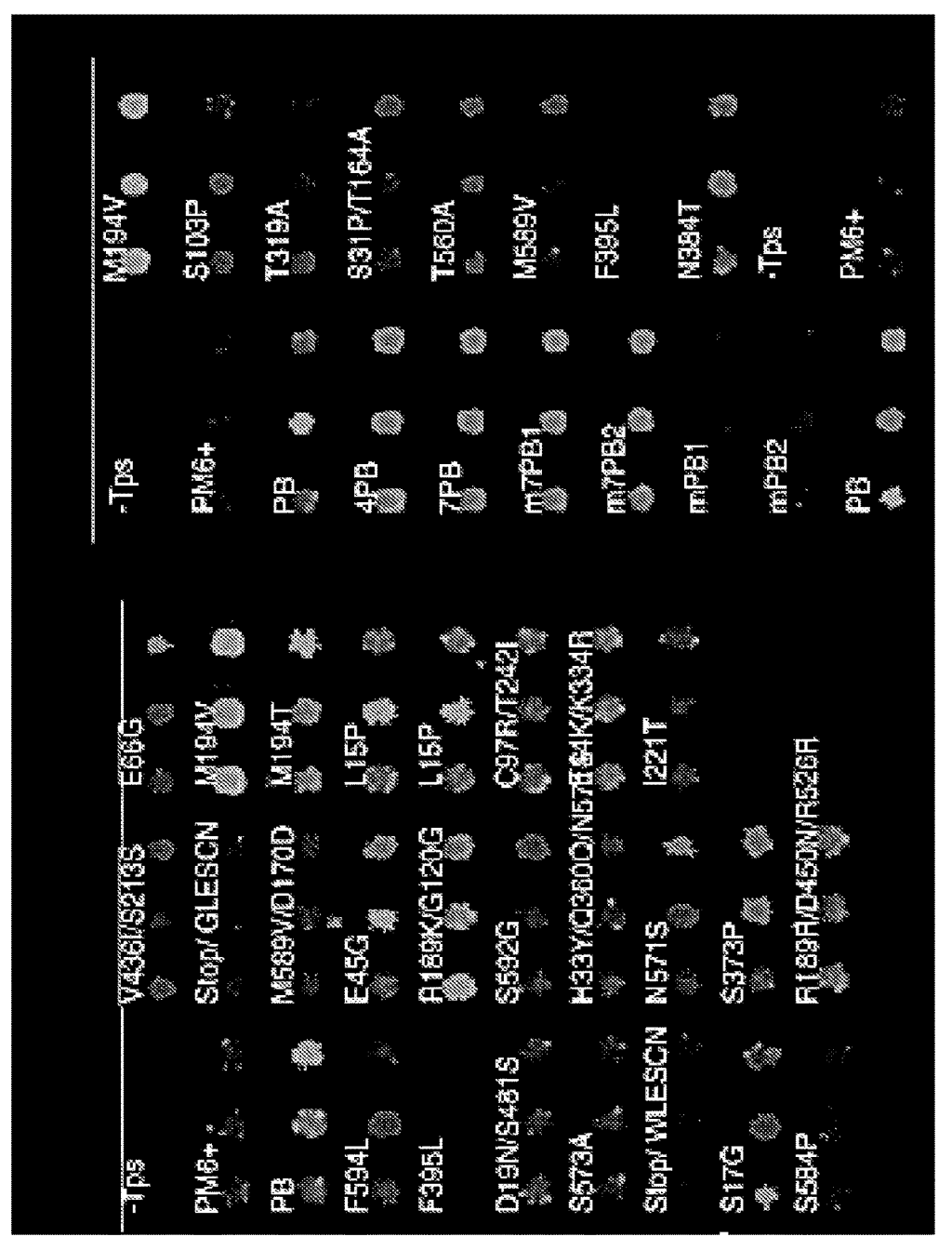
Figure 4C:
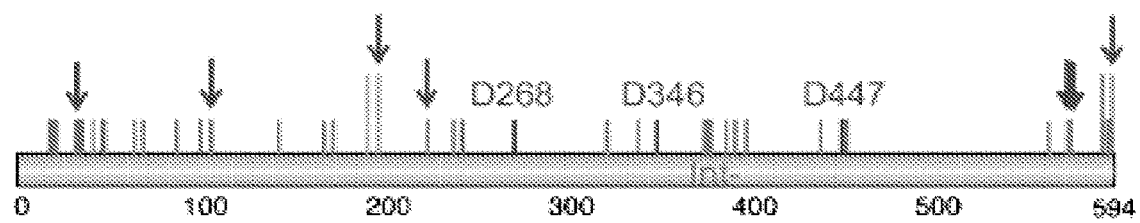
FIG. 4C shows the location of the 35 best candidates.

To more accurately measure the excision activity in vivo, we set up in vivo excision systems in both yeast *S. cerevisiae* and mammalian HEK293 cells. In yeast system, we cloned the piggyBac transposon carrying a kanamycin marker into the mCherry gene at TTAA site located at the very N-terminus of the mCherry gene (position 80-83) on pGAP/Cherry plasmid (9). This disrupts the expression of red fluorescence protein (RFP) (FIG. 4A). The mCherry gene will be fully restored in the presence of piggyBac transposase, which can be precisely excised and repaired. RFP signal can be detected under fluorescence microscope (Leica: M165FC). We transformed both WT and R372A/K375A mutants in a pGals expression vector into yeast strain BY4727 with plasmid pCherry::PBTn, 3 days later, colonies were re-suspended in water and spotted onto both SC (synthetic complete) media Trp-Ura+Glucose and Galactose plates. Re-plating plates were scanned under the fluorescence microscope 1, 2 and 3 days later. From FIG. 4B, we can observe that the excision activity of R372A/K375A mutant was weaker than WT, which is in agreement with the in vitro results.

Excision and Integration Assay in Mammalian Cells

Figure 5A:
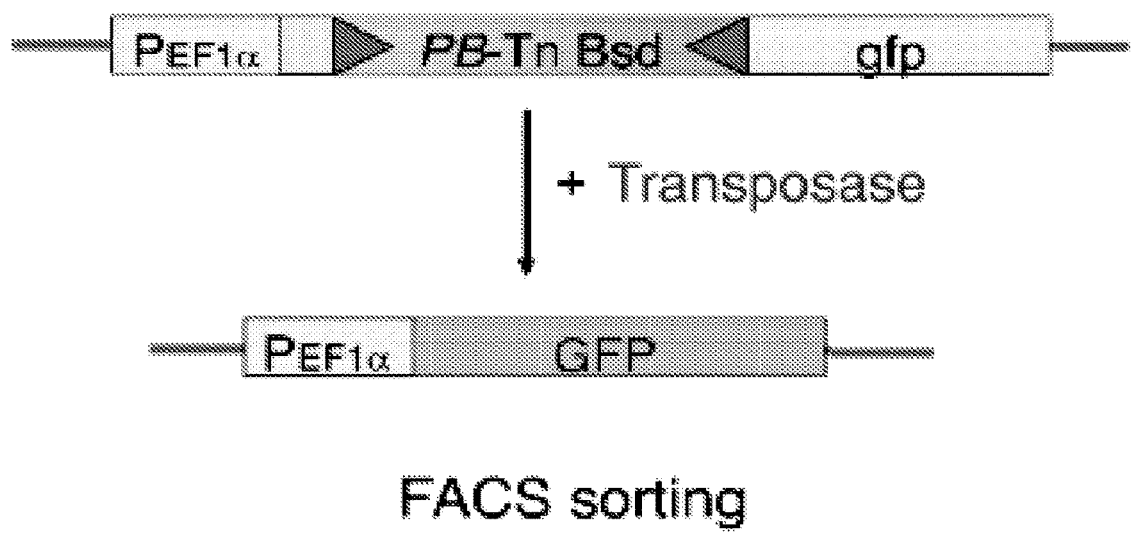
FIG. 5A shows a diagram of the test strategy for testing the relative excision activities of the hyper reactive R372A/K375A transposase mutants in mammalian cells.

A similar strategy was used to measure the excision activity in HEK293 cells. First, we generated a stable HEK293 cell line by Tol2 transposition, in which a Tol2 transposon carrying the Cycle 3-GFP (C3-GFP) under the control of EF-Iα promoter. The C3-GFP gene was first mutated at position 72 from T to C of the C3-GFP gene by site-directed mutagenesis which created a HpaI site for cloning of the piggyBac transposon which carries a blasticidin drug resistance gene. The Tol2 transposon will permanently integrate into the chromosome in the presence of Tol2 transposase. With this strategy, we generated a stable cell line—HEK293/T46—to use in mammalian cell excision. Once the piggyBac transposon is excised by piggyBac transposase, the C3-GFP gene will be restored and the GFP signal can be sorted by FACS (fluorescence activated cell sorter) analysis as shown in FIG. 5A). To compare the R372A/K375A mutant with WT in excision activity, we transiently transfected plasmids of R372A/K375A mutant and WT in pcDNA3.1/myc-HisA mammalian expression vector into HEK293/T46 line which carries C3-GFP::PBTn. Four to five days later, cells were trypsinized and washed with PBS. Then FACS analysis was used to measure the GFP cell population. As showed in FIG. 5B, we also observed the R372A/K375A mutant has about 50-60% of WT excision activity.

Screening Hyperactive piggyBac/Exc$^+$Int$^-$ Mutants in *S. cerevisiae*.

To make a more efficient tool for piggyBac transposon excision, we set up to screen excision hyperactive and integration negative mutants. First, we generated PB/R372A/K375A mutagenesis libraries with 2 primers: pGals-f for priming the 5'-side of the pGals vector cloning site sequence with ATG start codon of the transposase; the second primer, pGals-r for priming the 3'-side of the cloning site with TGA stop codon of the transposase. We used error-prone PCR in the presence of $Mn^{2+}$ to generate three mutagenesis libraries and then co-transformed with linearized pGals vector into *S. cerevisiae* BY4727/Cherry::PBTn. Through homologous recombination, the libraries were constructed in pGals vector in the strain containing Cherry::PBTn. Single colonies were picked and re-suspended in water in 96-well plates and pin replicated to SC-Trp-Ura+Glucose or Galactose omitray plates. Plates were grown at 30° C. for 1, 2, 3 and 4 days and scanned by typhoon scanner to see if any colonies showed more fluorescence at the RFP channel on both Glucose and Galactose plates or any of Glucose or Galactose plates. Plasmids were recovered from the yeast strains with Qiagen mini-prep kit and re-transformed into *E. coli* NEB5α. Colonies were sequenced at MCLAB with primers PGB340 and PGB341.

Figure 6A:
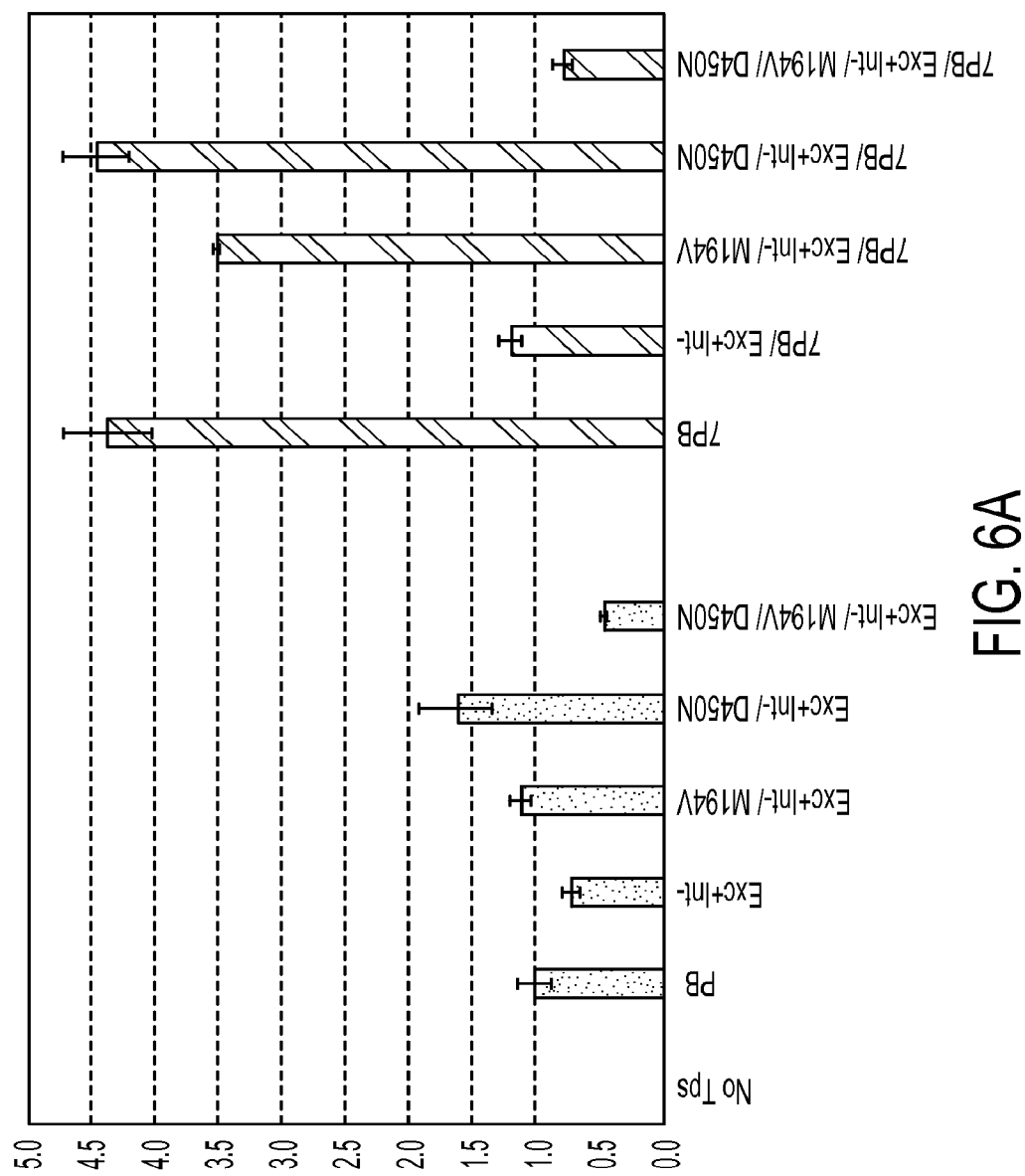
FIGS. 6A and 6B are bar graphs showing activity levels of a hyperactive transposase in bar graphs and FIG. 6C shows the actual cell colonies on plates.

We screened a total of 6000 colonies from three individual libraries and got 35 candidates to test for further confirmation in the yeast excision assay system. We also tested the candidates in mammalian cells HEK293/T46. As shown in FIG. 5B, nine candidates showed higher excision activity than R372A/K375A; they are S103P/R372A/K375A, M194V/R372A/K375A, M194T/R372A/K375A, I221T/R372A/K375A, T560A/R372A/K375A, S573AJR372A/K375A, M589V/R372A/K375A, S373P/R372AJK375A, D450N/R372A/K375A. As two candidate mutants—M194V/R372A/K375A and D450N/R372A/K375A—showed the highest excision rates, we focused on these two mutants and asked whether we could make them more hyperactive by combining these two mutants into one, or combine them separately or together with 7PB, a combination hyperactive mutant from WT piggyBac transposase screening (10). As shown in FIG. 6A, when combining M194V and D450N together with R372A/K375A into one ORF, the excision activity went down to about WT PB level. When combining M194V/R372A/K375A or D450N/R372A/K375A with 7PB, much higher (5-6 fold) excision activity as compared with R372A/K375A was observed. However, when we combined 7PB, M194V, D450N and R372A/K375A all in one, the excision activity decreased to WT level. This result suggests that certain combination of hyperactive mutants might not be better than each one alone of them in excision activity.

Figure 6B:
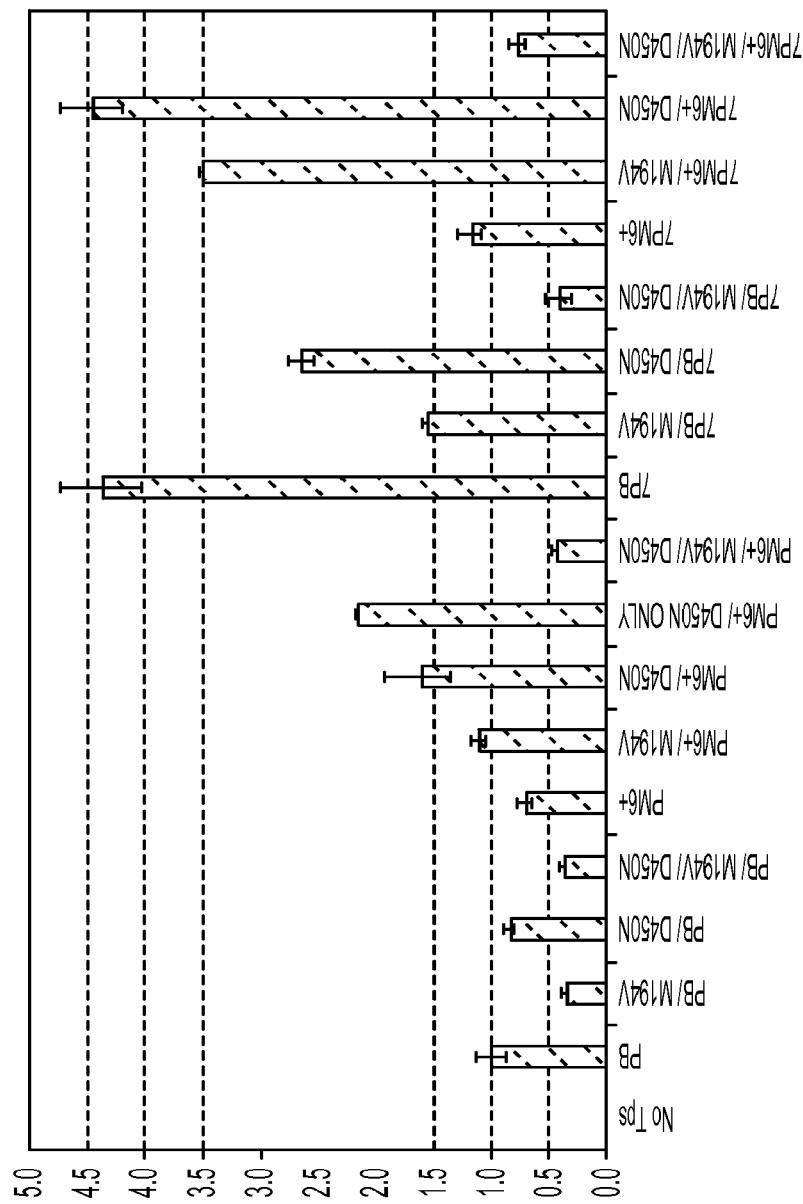
Figure 6C:
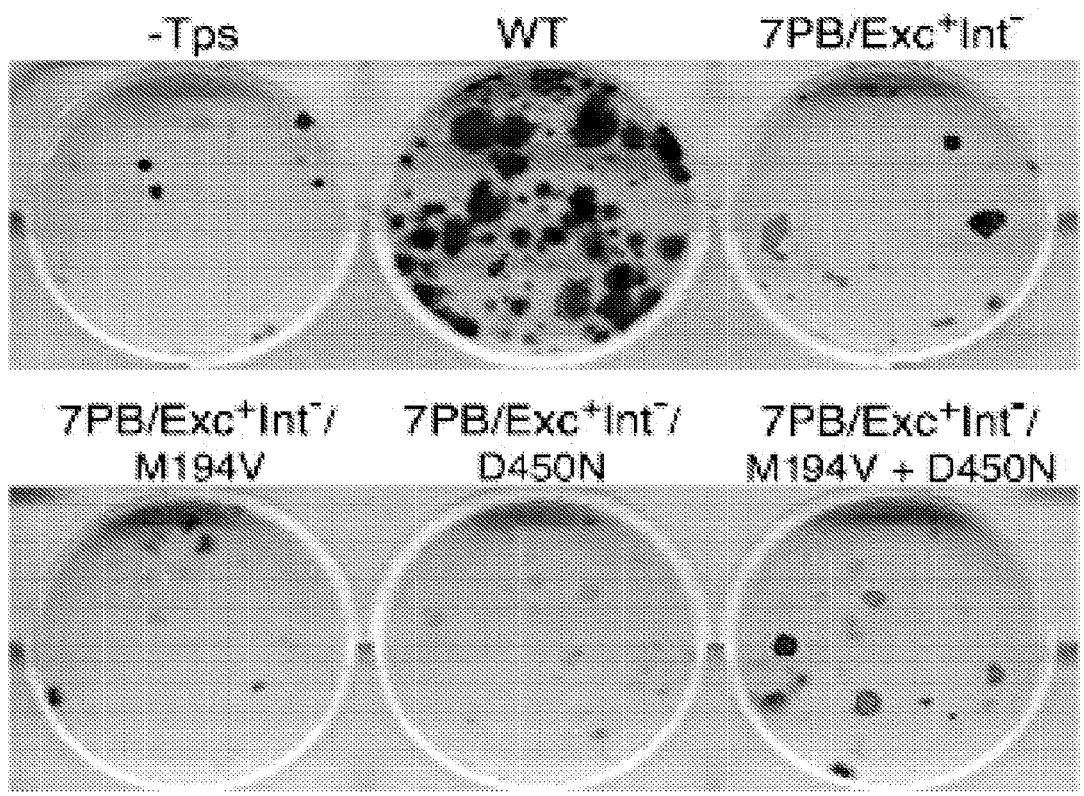

We also tested the integration activity of 7PB/R372A/K375A/M194V and 7PB/R372A/K375A/D450N to make sure none of the combination recovered the integration activity. As shown in FIG. 6B, they did not show increases in integration.

Shuffle-PCR to Screen Different Mutant Combination.

Figure 7A:
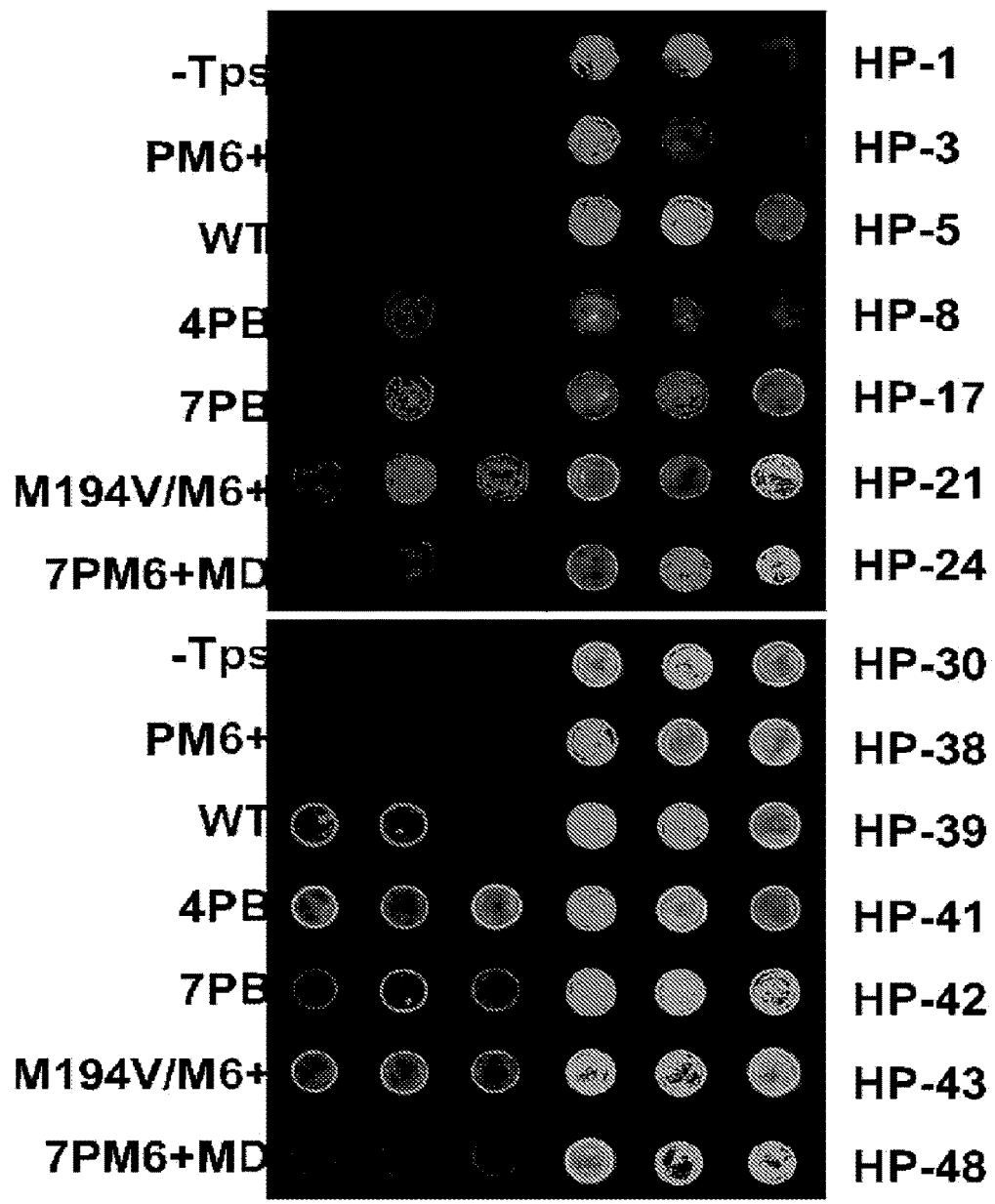
FIG. 7A shows results of a retest in yeast cells demonstrating that the mutants are still defective in integration.
Figure 7B:
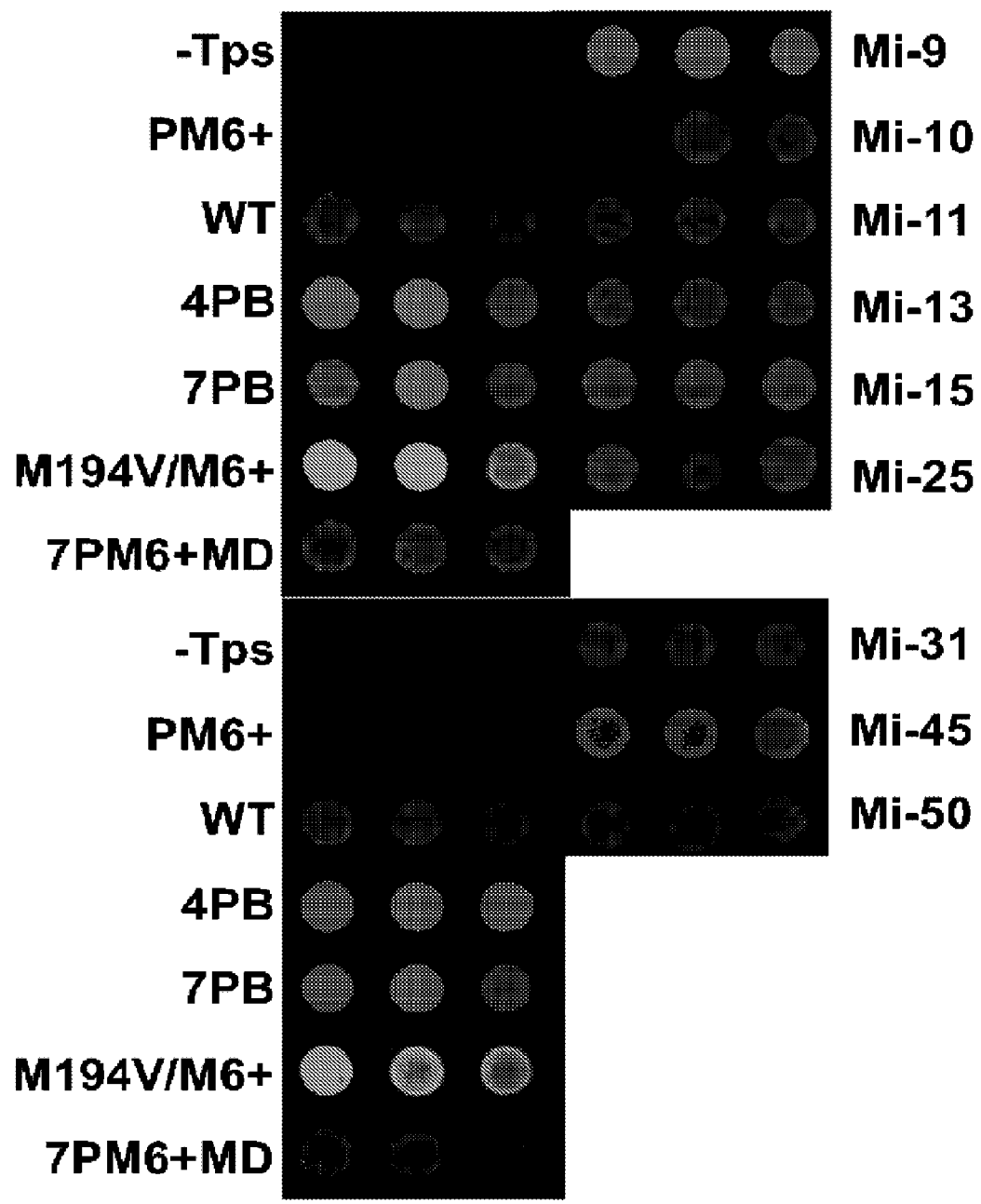
FIG. 7B shows similar results for mutation combinations.
Figure 8:
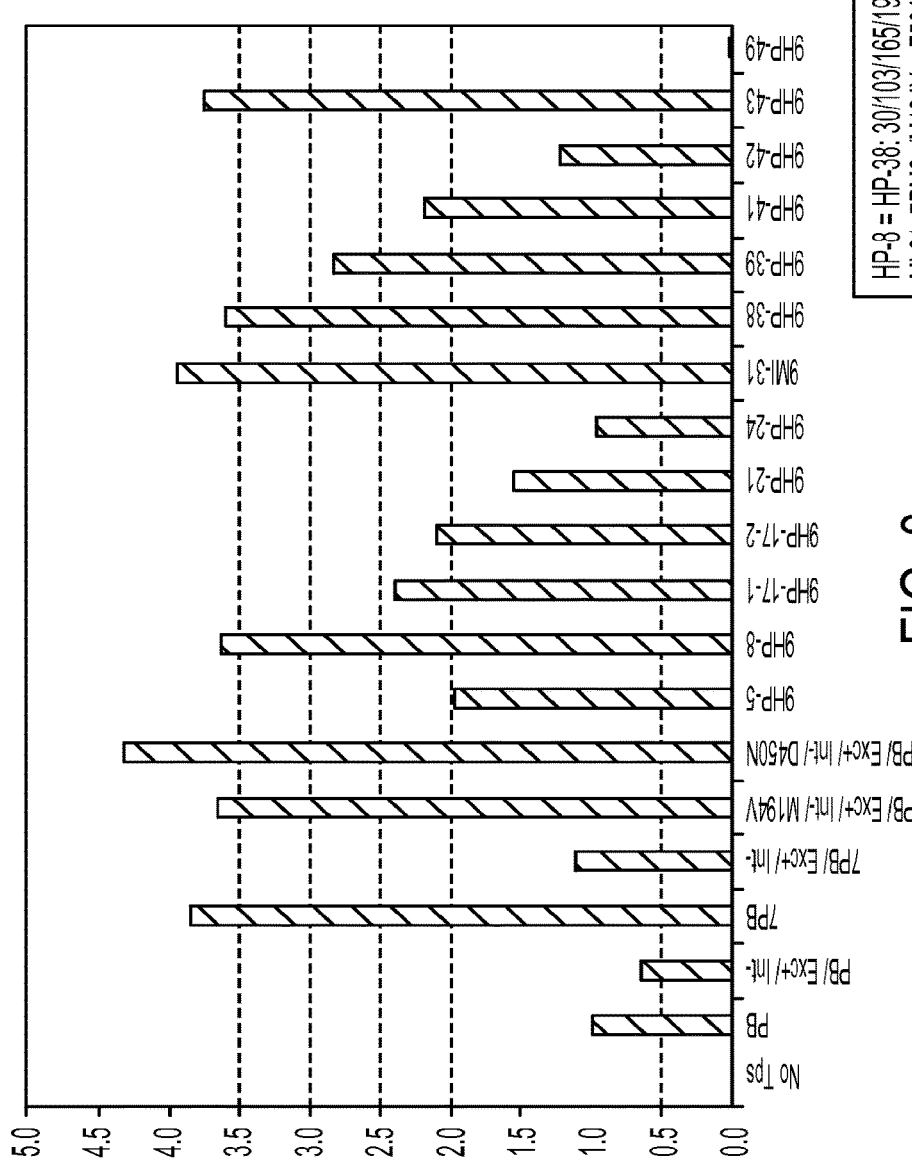
FIG. 8 is a bar graph showing retest in mammalian cells of mutant combinations demonstrating hyperactive excision.

Next we performed a shuffling-PCR screening of the nine different amino acids with R372A/K375A to see which one gave the highest activity. To get all possible combinations of 511 mutants, we used a Shuffle-PCR strategy. Briefly, the first 100 cycle is based on limiting amounts of PCR primers versus two templates: WT with R372A/K375A and all nine amino acid mutations with R372A/K375A at ratio 1:1, 2:1 and 1:2. We used a very short extension time, denatured immediately at 95° C., and then annealed to make them switch templates as described below in materials and methods. Homologous recombination in yeast cell with pGals linearized vector and gel purified Shuffle-PCR generated PCR products were transformed into yeast strain BY4727/Cherry::PBTn. Single colonies were picked and resuspended in water and spotted to SC-TRP-URA+Gal plates. One day after 30° C. culture, the plates were scanned for intensity of RFP of the spot. WT PB, PB/R3 72A/K3 7 5A, PB/R372A/K375A/M194V, PB/R3 72A/K3 75A/D45 0N, 7PB/R372A/K375A/M194V+D450N and 7PB, a hyperactive from previous screening in our lab (10) were used as control. Among these controls, PB/R372A/K375A/M194V gives strongest signal. The colonies with increased intensity of RFP signal as compared with PB/R372A/K375A/M194V were chosen and plasmids were recovered, sequenced re-transformed into yeast BY4727/pGAPCherry::PBTn and retested for fluorescence. Because some of the mutants showed fluorescence earlier due to the early excision that occurred in specific colonies, especially with hyperactive mutants, retest can tell the real hyperactive mutants. As shown in FIG. 9A and FIG. 7A, some of the mutant combinations with R372A/K375A show hyperactive excision. FIG. 9B and FIG. 7B show mutant combinations with R372A/K375A give excision activity at around WT PB level. FIG. 9C shows mutant combinations with R372A/K375A that give low excision activity. We then tested the mutant combinations shown in FIG. 9A in mammalian cell HEK293/T46. Unfortunately, as shown in FIG. 8, none of them showed higher activity than 7PB/R372A/K375A/D450N, but HP-8, HP-31, HP-38 and HP-43 showed moderately higher activity than 7PB/R372A/K375A/M194V and 7PB. Since we did not run the FACS at the optimum filter setting (excitation 395 nm, emission 507 nm) for C3-GFP, the difference between different mutants might be enhanced by changing the filter setting.

Materials and Methods

```
Primers for making Exc+Int- mutant candidates:
M1 (R245A) 54 mer, aga to gca, 5'-gagaaaac gatgtat
ttactcctgttgcaaaaatatgggatctattatccatcag-3' [SEQ
ID NO: 4](5'-ctgatggataaagagatcccatattttttgcaacagga
gtaaatacatcgttttctc-3' [SEQ ID NO: 5])

M2 (R275A/ R277A) 64 mer aga to gca/ cgg to gcc
5'-gaccatagatgaacagttacttggttttgcaggagcctgtccgttta
ggatgtatatccc-3' [SEQ ID NO: 6] (5'-gggatatacatcct
aaacggacaggctcctgcaaaaccaagtaactgttcatctatggtc-3'
[SEQ ID NO: 7])

M3 (K287A) 55 mer aag to gcg 5'-ccgtttaggatgtatatc
ccaaacgcgccaagtaagtatggaataaaaatcc-3' [SEQ ID NO:
8] (5'- ggattttattccatacttacttggccgcgtttgggatatac
atcctaaacgg-3' [SEQ ID NO: 9])

M3+ (K290A) 55 mer aag to gcg/ aag to gcg
5'-gtatatcccaaacgcgccaagtgcgtatggaataaaaatcctcatga
tgtg-3' [SEQ ID NO: 10] (5'-cacatcatgaggattttattc
cataggcacttggcttgtttgggatatac-3' [SEQ ID NO: 11])

M4 (R315A) 47 mer aga to gca 5'-gataaatggaatgcctta
tttgggagcaggaacacagaccaacggag-3' [SEQ ID No: 12]
(5 gttggtctgtgttcctgctccc aaataaggcattccatttatcata
t-3' [SEQ ID NO: 13])

M5 (R341A) 40 mer cgt to gct 5'-gcctgtgcacggtagttg
tgctaatattacgtgtgacaattggttcac-3' [SEQ ID NO: 14]
(5'-gtgaaccaattgtcacacgtaatattagcacaactaccgtgcacag
gc-3' [SEQ ID NO: 15])

M6 (R372A) 35 mer cga to gca/ aaa to gca 5'- gtggg
aaccgtgcgatcaaacgcacgcgagataccggaagtac-3' [SEQ ID
NO: 16] (5'-gtacttccggtatctcgcgtgcgtttgatcgcacggtt
cccac-3' [SEQ ID NO: 17])

M6+ (R372A/ K375A) 36 mer 5'-gttaaccattgtgggaac
cgtggcatcaaacaaacgcgagataccttaac-3' [SEQ ID NO:
18] (5'-ggtatctcgcgtttgtttgatgccacggttcccacaatg
g-3' [SEQ ID NO: 19])

M7 (R388A) 39 mer agg to gcc 5'-gtactgaaaaacagtcgc
tccgcccagtgggaacatcgatg-3' [SEQ ID NO: 20] (5'-ca
tcgatgttcccactggggcggagcgactgttttttcagtac-3' [SEQ
ID NO: 21])

M8 (K412A) 53 mer aag to gcg 5'-ctcatataaaccgaagcc
agctgcgatggtatacttattatcatcttgtg-3' [SEQ ID NO:
22] (5'-cacaagatgataataagtataccatggcagctggcttcggtt
tatatgag-3 [SEQ ID NO: 23])

M8+ (K409A/ K412A) 53 mer aag to gcg/ aag to gcg
5'-cttactctcgtctcatataaaccggcgccagctgcgatggtatactt
a-3' [SEQ ID NO: 24] (5'-ataataagtataccatcttagctgg
ggccggtttatatgagacgagagtaagg-3' [SEQ ID NO: 25])

M9 (K432A) 43 mer aaa to gca 5'-cttctatcaacgaaagta
ccggtgcaccgcaaatggttatgtattataatc-3' [SEQ ID NO:
26] (5'-taaccatttgcggtgcaccggtactttcgttgatagaagcat
c-3' [SEQ ID NO: 27])

M10 (R460A/ K461A) 58 mer agg to gcg/ agg to gcg
5'-ccaaatgtgttctgtgatgacctgcagtgcggcgacgaataggtggc
ctatggcattattg-3' [SEQ ID NO: 28] (5'-caataatgccat
aggccacctattcgtggcggcactgcaggtcatcacagaacacatttgg-
3' [SEQ ID NO: 29])
```

-continued

M11 (R499A0 61 mer cgc to gcc (not include in the data) 5'-cagtagcaagggagaaaaggttc aaagtgc cgc aaaat ttatgagaaac ctttac atg agcctg-3' [SEQ ID NO: 30] (5'-caggctcatgtaaaggtttctcataaattttgcggcactttgaacc ttttctcccttgctactg-3' [SEQ ID NO: 31])

M12 (R518A) 42 mer cgt to gct (not include in the data) 5'-gacgtcatcgtttatgcgtaaggctttagaagctcctactt tgaagag-3' [SEQ ID NO: 32] (5'-ctcttcaaagtaggagctt ctaaagccttacgcataaacgatgacgtc-3' [SEQ ID NO: 33])

Excision assay primers:
pbexl2, GGAACAGGAGAGCGCACGAG [SEQ ID NO: 34]

pbexr2, GAGAGTGCACCATATATGCGGTG [SEQ ID NO: 35]

piggyBac Exc+Int- mutant random mutagenesis library PCR primers:
pGals-f, 57-mer CTTTAACGTCAAGGAGAAAAAACCCCGGATTCTA GAACTAGTGGAT CCCCCGGGatg [SEQ ID NO: 36]

pGals-r, 58 mer GATGTGGGGGAGGGCGTGAATGTAAGCGTGACA TAACTAATTACATGACTCGAGtca [SEQ ID NO: 37]

pGals piggyBac mutants sequencing primers:
GTATTACTTCTTATTCAAATG [SEQ ID NO: 38]

TCAGGTTGTCTAACTCCTTCC [SEQ ID NO: 39]

Plasmid Constructions

Mammalian expression vectors of the piggyBac transposase and its mutants were constructed by PCR. The transposases ORFs (PB-f (KpnI+Kozak) GAggtaccGC-CACCATGGGTAGTTCTTTAGACGATGAG [SEQ ID NO:40] and PB-4r (NotI, with stop) CAGgcggccg ctcaGAAACAACTTTGGCACATATCAATATTATG [SEQ ID NO:41] with KpnI and NotI sites) were cloned into KpnI and NotI sites of pcDNA3.1/myc-HisA vector (Invitrogen). Excision+ integration- mutant candidates were obtained by site-directed mutagenesis.

The piggyBac transposon plasmids for mammalian cell integration assay contain a green fluorescent protein (Cycle 3-GFP) and blasticidin resistance (BsdR) cassette driven by a CMV promoter, flanked by 662 bp Left and 394 bp Right end sequences.

Plasmids for expression of piggyBac transposase and excision[+] integration[-] candidates were constructed in pET22b+(EMD) (PB-112 (NdeI) CAGcat atgGGTAGTTCTTTAGACGATGAGC [SEQ ID NO:42] and PB-2r (XhoI, no stop codon) CAGctcgag GAAACAACTTTGGCACATATCAATATTATGC [SEQ ID NO:43] and cloned in NdeI, XhoI sites without stop codon, which will give (extra peptide: LEHEITIHHH (SEQ ID NO:51)) C-terminal His-tag.

For yeast hyperactive color screening plasmid Cherry:: PBTnKan construct, pYeGAP-Cherry was obtained by homologue recombination with PCR amplified PBTnKan with homologous cherry oligos: TGGCTATTAT-TAAAGAATTTATGAGATTTAAAGTTCATATG-GAAGGTTCAGTT AACCCTAGAAAGATAGTCTGCG [SEQ ID NO:44] and CTTCATAT GGTCTACCTTCACCT-TCACCTTCAATTTCAAATTCATGACCATTAAC-CCTAGA AAGATAATCATATT [SEQ ID NO:45]. G418 colonies were picked and determined by sequencing. The PBTnKan was introduced at position 80-83 TTAA site of the Cherry gene.

For Making Mammalian Hyperactive Color Assay Plasmid

The pC3GFP::PBTnBsd. Cycle 3-GFP gene from pTracer-CMV/Bsd (Invitrogen) was site-directed mutagenized at position 72 from T to C with primer C3GFHpa CAATTCTTGTTGAATTAGATGGTGATGT-TAACGGGCACAAATTTTCTG TCAGTGG [SEQ ID NO:46] and its complimentary strand, which will generate a HpaI site. The piggyBac transposon carries a blasticidin resistance gene flanked by 662 by L-end and 394 by R-end sequences with blunt HpaI ends at both 3' and 5' ends that was introduced by ligation. Primers with BseRI and NotI were used to PCR the EFIα promoter with the Cycle 3-GFP::PBTnBsd out and clone into pCMV/Zeo (Invitrogen). This creates the plasmid of pEF/C3-GFP::PBBsd. To12 transposon L-end 318 by (ApaI, NotI) and R-end 302 bp (Psd, Nad) were introduced by PCR To12 L- and R-ends as well as pCMV/Amp+pUC Ori with primers Tol2L (NotI), GAgcggccgcGTCTGACCAATTTCATATAATGTG [SEQ ID NO:47] and Tol2R (Sbt1), GAcctgca ggCATTAGATTGTCTGTCTTATAGTTTG [SEQ ID NO:48]. Cut with SbfI and NotI, ligated to SbfI+NotI fragment pEF/C3-GFP::PBBsd containing EF1a/C3-GFP:: PBBsd. This will generate the final plasmid for generating stable cell lines by Tol2 transposition. pGalsPB/R372A/ K375A, pGalsPB, pGals7PB were cloned into pGals vector at XmaI and XhoI sites.

Methods

Mammalian Cell Culture and Excision and Integration Assay

HEK293 and HeLa cells were cultured in DMEM supplemented with 5% FBS and 2 mM L-glutamine. For excision assay by PCR, about $2 \times 10^6$ HEK293 cells were transfected with 1.6 μg of transposon plasmid—pCMV/PBGB and 0.4 μg of transposase and mutant plasmids with FuGENE 6 transfection reagent (Roche Applied Science). Three days later, cells were harvested and plasmids were recovered by Hirt methods (5). The mixtures (helper, donor, repaired donor plasmids) were used as template to perform PCR with two primers against the flanking donor sides of donor plasmid (pbexl2 and pbexr2) with PCR cycles (94° C., 4 mM; 40 cycle of 94° C., 30 sec, 65° C., 30 sec, 72° C., 45 sec; 72° C., 10 min). Reaction mixture: water 30.5 μl, 10× buffer 5 μl, 10 mM dNTP 1 μl, 20 μM Pbex12, 5μ1, 20 μM Pbexr2, 5μ1, Hirt method recovered DNA 2 μl, High Fidelity Taq DNA polymerase 1 μl) with Expand High Fidelity PCR system (Roche). PCR products were run on 1% agarose gel.

For integration assay, $3\text{-}5 \times 10^5$ HeLa cells were transfected with 1.6 μg of transposon plasmid—pCMV/PBGB and 0.4 μg of transposase and mutant plasmids with FuGENE 6 transfection reagent (Roche Applied Science). Two days later, cells were trypsinized and diluted to different dilution and continued culturing in DMEM containing 3.5 μg/ml of blasticidin for 18-21 days. Medium was changed every 2-3 days. Surviving colonies were stained with 0.2% methylene blue. Plates were scanned with scanner.

Protein Expression, Purification and In Vitro Assay.

The piggyBac WT and mutant proteins were expressed in BL21 codon plus/DE3 RIL strain (Stratagene) in pET22b vector (Novagen) with C-terminal His-tag. Protein purification and in vitro nick, double-strand break, hairpin opening, strand-transfer assays have been described previously (4). For hairpin opening, a 74 nt oligo containing 35 bp of PB L-end and flanking TTAA in the middle (PGB40) was synthesized (IDT) and PAGE gel purified and labeled at the 5'-end with γ-$^{32}$P-ATP. Reactions were run as previously described and reactions were stopped with EDTA at 1, 3, 10 and 20 min.

For Strand-Transfer Assay:

R-end oligos PGB18 CCCTAGAAAGATAATCATATTGTGACGTACGTTAAAGATAATCATG CGTAAAATTGACGCATGTGTTTT [SEQ ID NO:49] and its complimentary strand PGB19 TTAAAACACATGCGTCAATTTTACGCATGATTATCTTTAACGTACGT CACAATATGATTATCTTTCTAGGG [SEQ ID NO:50] were annealed and labeled at 5'-end with γ-$^{32}$P-ATP on both strands. Reactions were run as previous described and reactions were stopped with EDTA at 1, 3, 10 and 20 min.

Hyperactive PB/Exc$^+$Int$^-$ Mutants Screening in Yeast

The yeast strain BY4727 has been described previously (4). Donor plasmid pGAP-Cherry::PBTnKan (URA+) was used in this study. Random mutagenesis libraries of PB/Exc+Int– transposase gene was carried out by error-prone PCR in the presence of manganese and the resulting mutant pools were introduced into a linearized pGALS vector (TRP+) by homologous recombination in yeast. Transformant colonies were grown for three days, resuspended in water and spotted onto SC plates lacking tryptophan and uracil and with 2% galactose (SC-Trp-Ura+Gal) for transposase induction. The piggyBac excises precisely, allowing us to directly evaluate transposon excision from a gene encoding a RFP in a two-plasmid system. The transposon donor plasmid contained a yeast maximized DsRed RFP gene (9) in which the piggyBac transposon described above was flanked by TTAA at RFP by 80-83. S. cerevisiae BY4727 containing this donor plasmid are non-fluorescent. Galactose induction of the transposase from the helper plasmid results in precise excision and colony fluorescence that can be detected using a fluorescence microscope (Leica: M165FC). To screen for hyperactive mutants, we mutagenized the piggyBac/R372A/K375A ORF by amplification with error-prone MnCl$_2$ PCR with primers from the pGalS promoter and CYCl terminator region and introduced the PCR product by homologous recombination into pRS414 linearized by XmaI-XhoI digestion into strain BY4727 containing pGAP-Cherry::PBTnKan. More than six thousand individual transformants were picked in 96 well format on SC (synthetic complete) media containing galactose. We scored transposition by looking for increased fluorescence over 1-3 days, and about 35 hyperactive candidates were found. Yeast plasmid DNAs were isolated and the mutant PB/Exc+Int– ORFs were sequenced and retested in BY4727 containing pGAP-Cherry::PBTnKan to exclude the earlier excision events.

Mammalian Excision Assay In Vivo.

For generating stable cell lines containing pEFIa/cyc-3-GFP::PBTnBsd, a To12 mediated transposition was used to integrate the DNA fragment into genomic DNA of HEK293 cells and colonies were picked and analyzed. To quantitatively analyze the relative excision activity of different mutants, a color (GFP) excision assay by FACS sorting was used. A HEK293 stable cell line containing pEFIa/cyc-3-GFP::PBTnBsd, T46 was used and transfected with PB transposase and different mutant plasmids with FuGENE 6 transfection reagent (Roche Applied Science). Four days later, cells were trypsinized and FACS analyzed with BD FACSCalibur (BD Biosciences, 488 nm excitation, 509 nm emission not the best for cycle-3 GFP, should use exc 395 nm, 507 nm) to see the percentage of GFP cell population in the whole cell population. Data were analyzed with FlowJo 8.5.3. GFP positive cells were counted against whole cells. GFP cells from WT PB were used to standardize that from mutant PB/Exc+Int–. To detect fluorescent cells, it is important to pick the best filter set to optimize detection. The primary excitation peak of cycle-3 GFP is at 395 nm. There is a secondary excitation peak at 478 nm. Excitation at either of these wavelengths yields a fluorescent emission peak with a maximum at 507 nm. Note that the quantum yield can vary as much as 5- to 10-fold depending on the wavelength of light that is used to excite the GFP fluorophore.

Shuffle-PCR:

To generate a library of nine mutations locate at different positions of the PB gene, we used Shuffle-PCR to make different combination. The total number of possible combination is 511. To do the Shuffle-PCR, we used the same forward and reverse primers as we generated Exc+Int– random mutation library and 2:1, 1:1 and 1:2 ration of 2 different templates—PB/Exc+Int– and 7PB/Exc+Int–+ M194V+D450N with low primers/template ratio. The PCR cycle is as follow: 94° C., 4 min; 100 cycles of 94° C., 10 sec, 65° C., 20 sec, 72° C., 6 sec; 10 cycles of 94° C., 30 sec, 65° C., 30 sec, 72° C., 2.5 min; 72° C., 10 min. The PCR reaction mixture was cleaned up by Qiaquick PCR purification Kit (Qiagen). The whole elution was used as templates to amplified by normal PCR reaction. The product was digested by DpnI to remove any template DNA and then gel purified from 1% agarose gel with Qiaquick gel purification Kit (Qiagen). The same procedures were used as previously to generate combination mutation library in the yeast strain BY4727 with donor plasmid pGAP-Cherry::PBTnKan has been described previously. More than 1500 individual transformants were picked in 96 well format on SC media containing galactose. We scored transposition by looking for increasing fluorescence over 1-3 days, and about 50 hyperactive candidates were selected. Yeast plasmid DNAs were isolated and the mutant combination PB/Exc+Int–, ORFs were sequenced and re-tested in BY4727 containing pGAP–, Cherry::PBTnKan to exclude the earlier excision events. The ones still showed hyperactive activity in retest were further cloned into pcDNA3.1/myc-HisA mammalian expression vector and examined the relative excision activity in HEK293 stable cell line containing pEFIα/cyc-3-GFP::PBTnBsd, T46. Four days later, cells were trypsinized and FACS analyzed with BD FACSCalibur (BD Biosciences) to see the percentage of GFP cell population in the whole cell population. Data were analyzed with FlowJo 8.5.3. GFP positive cells were counted against whole cells. GFP cells from WT PB were used to standardize that from mutant PB/Exc+Int–.

Acknowledgement

The inventor is an Investigator of the Howard Hughes Medical Institute. This work was supported by Maryland Stem Cell Research Fund.

REFERENCES (1) Fraser M J, Ciszczon T, Elick T, Bauser C. Precise excision of TTAA-specific *lepidopteran* transposons piggyBac (IFP2) and tagalong (TFP3) from the baculovirus genome in cell lines from two species of *Lepidoptera*. Insect Mol Biol. 1996, 5 (2):141-51.

(2) Woltjen K, Michael I P, Mohseni P, Desai R, Mileikovsky M, Hamalainen R, Cowling R, Wang W, Liu P, Gertsenstein M, Kaji K, Sung H K, Nagy A. piggyBac transposition reprograms fibroblasts to induced pluripotent stem cells. Nature. 2009, 458 (7239):766-70.

(3) Yusa K, Rad R, Takeda J, Bradley A. Generation of transgene-free induced pluripotent mouse stem cells by the piggyBac transposon. Nat Methods. 2009, 6 (5):363-9.
(4) Mitra R, Fain-Thornton J, Craig N L. piggyBac can bypass DNA synthesis during cut and paste transposition. EMBO J. 2008, 27 (7):1097-109.
(5) Ziegler K, Bui T, Frisque R J, Grandinetti A, Nerurkar V R. A rapid in vitro polyomavirus DNA replication assay. J Virol Methods. 2004 Dec. 1; 122 (1):123-7.
(6) Wang W, Lin C, Lu D, Ning Z, Cox T, Melvin D, Wang X, Bradley A, Liu P. Chromosomal transposition of PiggyBac in mouse embryonic stem cells. Proc Natl Acad Sci USA. 2008 Jul. 8; 105 (27):9290-5. Epub 2008 Jun. 25.
(7) Harper A L, Skinner L M, Sudol M, Katzman M. Use of patient-derived human immunodeficiency virus type 1 integrases to identify a protein residue that affects target site selection. J Virol. 2001 August; 75 (16):7756-62.
(8) Maertens G N, Hare S, Cherepanov P. The mechanism of retroviral integration from X-ray structures of its key intermediates. Nature. 2010 Nov. 11; 468 (7321):326-9.
(9) Keppler-Ross S, Noffz C, Dean N. A new purple fluorescent color marker for genetic studies in *Saccharomyces cerevisiae* and *Candida albicans*. Genetics. 2008 May; 179(1):705-10.
(10) Yusa K, Zhou L, Li M A, Bradley A, Craig N L. A hyperactive piggyBac transposase for mammalian applications. Proc Natl Acad Sci USA. 2011 Jan. 4. [Epub ahead of print]
(11) Chen Y T, Furushima K, Hou P S, Ku A T, Deng J M, Jang C W, Fang H, Adams H P, Kuo M L, Ho E N, Chien C L, Behringer R R. piggyBac transposon-mediated, reversible gene transfer in human embryonic stem cells. Stem Cells Dev. 2010 June; 19 (6):763-71.
(12) Stadtfeld M, Hochedlinger K. Without a trace? PiggyBac-ing toward pluripotency. Nat Methods. 2009 May; 6 (5):329-30.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. An improved *Trichoplusia ni* piggyBac transposase comprising a substitution at one or more of amino acid positions 245, 275, 277, 341, 372, 375, and 388 of SEQ ID NO: 52, wherein SEQ ID NO: 52 consists of amino acid residues 181-540 of the wild type *Trichoplusia ni* piggyBac transposase, and wherein the improved transposase exhibits enhanced piggyBac transposon excision activity and no or significantly diminished piggyBac transposon integration as compared to a wild type *Trichoplusia ni* piggyBac transposase.

2. The improved transposase according to claim 1, wherein an arginine at one or more of amino acid positions 245, 275, 277, 341, 372 and 388 is replaced with an alanine.

3. The improved transposase according to claim 1 wherein a lysine at amino acid position 375 is replaced with an alanine.

4. The improved transposase according to claim 1, wherein an arginine at amino acid position 275 is replaced with alanine and an arginine at amino acid position 277 is replaced with alanine.

5. The improved transposase according to claim 1, wherein an arginine at amino acid position 372 is replaced with alanine and a lysine at amino acid position 375 is replaced with alanine.

6. The improved transposase according to claim 1, wherein an arginine at amino acid position 388 is replaced with alanine.

7. A method of reversibly transforming a cell comprising the steps of:
   using a piggyBac transposon to insert a nucleic acid sequence into the genome of the cell thereby transforming the cell; and
   exposing the cell to the improved transposase of any one of claims 1, 2-3, and 4-6, thereby removing the nucleic acid sequence.

* * * * *

```
                        SEQUENCE LISTING

<160> NUMBER OF SEQ ID NOS: 52

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggaacaggag agcgcacgag                                                  20

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gagagtgcac catatatgcg gtg                                              23

<210> SEQ ID NO 3
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
catgcgtcaa ttttacgcag actatctttc tagggttaac cctagaaaga tagtctgcgt      60
aaaattgacg catg                                                        74

<210> SEQ ID NO 4
<211> LENGTH: 55
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 4
gagaaaacga tgtatttact cctgttgcaa aaatatggga tctattatcc atcag       55

<210> SEQ ID NO 5
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctgatggata aagagatccc atattttgc aacaggagta aatacatcgt tttctc       56

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaccatagat gaacagttac ttggttttgc aggagcctgt ccgtttagga tgtatatccc    60

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggatataca tcctaaacgg acaggctcct gcaaaaccaa gtaactgttc atctatggtc    60

<210> SEQ ID NO 8
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccgtttagga tgtatatccc aaacgcgcca agtaagtatg gataaaaat cc            52

<210> SEQ ID NO 9
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9 ggattttttat tccatactta cttggccgcg tttgggatat acatcctaaa cgg          53

<210> SEQ ID NO 10
<211> LENGTH: 51
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 10
gtatatccca aacgcgccaa gtgcgtatgg aataaaaatc tcatgatgt g         51

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cacatcatga ggatttttat tccataggca cttggcttgt ttgggatata c         51

<210> SEQ ID NO 12
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gataaatgga atgccttatt tgggagcagg aacacagacc aacggag              47

<210> SEQ ID NO 13
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gttggtctgt gttcctgctc ccaaataagg cattccattt atcatat              47

<210> SEQ ID NO 14
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcctgtgcac ggtagttgtg ctaatattac gtgtgacaat tggttcac             48

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtgaaccaat tgtcacacgt aatattagca caactaccgt gcacaggc             48

<210> SEQ ID NO 16
<211> LENGTH: 43
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 16
gtgggaaccg tgcgatcaaa cgcacgcgag ataccggaag tac          43

<210> SEQ ID NO 17
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtacttccgg tatctcgcgt gcgtttgatc gcacggttcc cac          43

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gttaaccatt gtgggaaccg tggcatcaaa caaacgcgag ataccttaac    50

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggtatctcgc gtttgtttga tgccacggtt cccacaatgg              40

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtactgaaaa acagtcgctc cgccccagtg ggaacatcga tg           42

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
catcgatgtt cccactgggg cggagcgact gttttcagt ac            42

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
ctcatataaa ccgaagccag ctgcgatggt atacttatta tcatcttgtg          50

<210> SEQ ID NO 23
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cacaagatga taataagtat accatggcag ctggcttcgg tttatatgag          50

<210> SEQ ID NO 24
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cttactctcg tctcatataa accggcgcca gctgcgatgg tatactta            48

<210> SEQ ID NO 25
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ataataagta taccatctta gctggggccg gtttatatga gacgagagta agg      53

<210> SEQ ID NO 26
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cttctatcaa cgaaagtacc ggtgcaccgc aaatggttat gtattataat c        51

<210> SEQ ID NO 27
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
taaccatttg cggtgcaccg gtactttcgt tgatagaagc atc                 43

<210> SEQ ID NO 28
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 28
ccaaatgtgt tctgtgatga cctgcagtgc ggcgacgaat aggtggccta tggcattatt    60
g                                                                   61

<210> SEQ ID NO 29
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
caataatgcc ataggccacc tattcgtggc ggcactgcag gtcatcacag aacacatttg    60
g                                                                   61

<210> SEQ ID NO 30
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cagtagcaag ggagaaaagg ttcaaagtgc cgcaaaattt atgagaaacc tttacatgag    60
cctg                                                                64

<210> SEQ ID NO 31
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caggctcatg taaaggtttc tcataaattt gcggcacttt gaaccttttc tcccttgct    60 actg                                                                64

<210> SEQ ID NO 32
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gacgtcatcg tttatgcgta aggctttaga agctcctact ttgaagag                48

<210> SEQ ID NO 33
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctcttcaaag taggagcttc taaagcctta cgcataaacg atgacgtc                48
```

-continued

```
<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggaacaggag agcgcacgag                                                   20

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gagagtgcac catatatgcg gtg                                               23

<210> SEQ ID NO 36
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ctttaacgtc aaggagaaaa aacccgggat tctagaacta gtggatcccc cgggatg          57

<210> SEQ ID NO 37
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gatgtggggg gagggcgtga atgtaagcgt gacataacta attacatgac tcgagtca         58

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtattacttc ttattcaaat g                                                 21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tcaggttgtc taactccttc c                                                 21

<210> SEQ ID NO 40
```

```
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gaggtaccgc caccatgggt agttctttag acgatgag                              38

<210> SEQ ID NO 41
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
caggcggccg ctcagaaaca actttggcac atatcaatat tatg                       44

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cagcatatgg gtagttcttt agacgatgag c                                     31

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cagctcgagg aaacaacttt ggcacatatc aatattatgc                            40

<210> SEQ ID NO 44
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tggctattat taaagaattt atgagattta aagttcatat ggaaggttca gttaacccta      60
gaaagatagt ctgcg                                                       75

<210> SEQ ID NO 45
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cttcatatgg tctaccttca ccttcacctt caatttcaaa ttcatgacca ttaaccctag      60
aaagataatc atatt                                                       75
```

<210> SEQ ID NO 46
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
caattcttgt tgaattagat ggtgatgtta acgggcacaa attttctgtc agtgg          55

<210> SEQ ID NO 47
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gagcggccgc gtctgaccaa tttcatataa tgtg                                 34

<210> SEQ ID NO 48
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gacctgcagg cattagattg tctgtcttat agtttg                               36

<210> SEQ ID NO 49
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ccctagaaag ataatcatat tgtgacgtac gttaaagata atcatgcgta aaattgacgc     60
atgtgttttt                                                            69

<210> SEQ ID NO 50
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ttaaaacaca tgcgtcaatt ttacgcatga ttatctttaa cgtacgtcac aatatgatta     60
tctttctagg g                                                          71

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Glu His Glu Ile Thr Ile His His His
1               5                   10

<210> SEQ ID NO 52
<211> LENGTH: 360
<212> TYPE: PRT
<213> ORGANISM: Trichoplusia ni

<400> SEQUENCE: 52

Gly Ile Leu Val Met Thr Ala Val Arg Lys Asp Asn His Met Ser Thr
1               5                   10                  15

Asp Asp Leu Phe Asp Arg Ser Leu Ser Met Val Tyr Val Ser Val Met
                20                  25                  30

Ser Arg Asp Arg Phe Asp Phe Leu Ile Arg Cys Leu Arg Met Asp Asp
            35                  40                  45

Lys Ser Ile Arg Pro Thr Leu Arg Glu Asn Asp Val Phe Thr Pro Val
        50                  55                  60

Arg Lys Ile Trp Asp Leu Phe Ile His Gln Cys Ile Gln Asn Tyr Thr
65                  70                  75                  80

Pro Gly Ala His Leu Thr Ile Asp Glu Gln Leu Leu Gly Phe Arg Gly
                85                  90                  95

Arg Cys Pro Phe Arg Met Tyr Ile Pro Asn Lys Pro Ser Lys Tyr Gly
            100                 105                 110

Ile Lys Ile Leu Met Met Cys Asp Ser Gly Thr Lys Tyr Met Ile Asn
        115                 120                 125

Gly Met Pro Tyr Leu Gly Arg Gly Thr Gln Thr Asn Gly Val Pro Leu
130                 135                 140

Gly Glu Tyr Tyr Val Lys Glu Leu Ser Lys Pro Val His Gly Ser Cys
145                 150                 155                 160

Arg Asn Ile Thr Cys Asp Asn Trp Phe Thr Ser Ile Pro Leu Ala Lys
                165                 170                 175

Asn Leu Leu Gln Glu Pro Tyr Lys Leu Thr Ile Val Gly Thr Val Arg
            180                 185                 190

Ser Asn Lys Arg Glu Ile Pro Glu Val Leu Lys Asn Ser Arg Ser Arg
        195                 200                 205

Pro Val Gly Thr Ser Met Phe Cys Phe Asp Gly Pro Leu Thr Leu Val
210                 215                 220

Ser Tyr Lys Pro Lys Pro Ala Lys Met Val Tyr Leu Leu Ser Ser Cys
225                 230                 235                 240

Asp Glu Asp Ala Ser Ile Asn Glu Ser Thr Gly Lys Pro Gln Met Val
                245                 250                 255

Met Tyr Tyr Asn Gln Thr Lys Gly Gly Val Asp Thr Leu Asp Gln Met
            260                 265                 270

Cys Ser Val Met Thr Cys Ser Arg Lys Thr Asn Arg Trp Pro Met Ala
        275                 280                 285

Leu Leu Tyr Gly Met Ile Asn Ile Ala Cys Ile Asn Ser Phe Ile Ile
290                 295                 300

Tyr Ser His Asn Val Ser Ser Lys Gly Glu Lys Val Gln Ser Arg Lys
305                 310                 315                 320

Lys Phe Met Arg Asn Leu Tyr Met Ser Leu Thr Ser Ser Phe Met Arg
                325                 330                 335

Lys Arg Leu Glu Ala Pro Thr Leu Lys Arg Tyr Leu Arg Asp Asn Ile
            340                 345                 350

```
Ser Asn Ile Leu Pro Asn Glu Val
    355                 360
```